(12) United States Patent
Hamada et al.

(10) Patent No.: US 8,356,525 B2
(45) Date of Patent: Jan. 22, 2013

(54) ANALYZER AND TRANSPORTATION DEVICE

(75) Inventors: Yuichi Hamada, Kobe (JP); Kunio Ueno, Kakogawa (JP)

(73) Assignee: Sysmex Corporation, Kobe (JP)

( * ) Notice: Subject to any disclaimer, the term of this patent is extended or adjusted under 35 U.S.C. 154(b) by 607 days.

(21) Appl. No.: 12/399,515

(22) Filed: Mar. 6, 2009

(65) Prior Publication Data
US 2009/0223311 A1 Sep. 10, 2009

(30) Foreign Application Priority Data
Mar. 7, 2008 (JP) .................................. 2008-057382

(51) Int. Cl.
*B01L 3/02* (2006.01)
(52) U.S. Cl. ....................................... 73/864.21; 422/653
(58) Field of Classification Search ........................ None
See application file for complete search history.

(56) References Cited

U.S. PATENT DOCUMENTS

| | | | |
|---|---|---|---|
| 3,897,216 A * | 7/1975 | Jones ............................ | 422/561 |
| 5,623,415 A | 4/1997 | O'Bryan et al. | |
| 6,117,392 A | 9/2000 | Hanawa et al. | |
| 6,290,907 B1 | 9/2001 | Takahashi et al. | |
| 7,264,111 B2 | 9/2007 | Veiner | |
| 7,283,217 B2 | 10/2007 | Ikeuchi et al. | |
| 7,910,067 B2 * | 3/2011 | Knight et al. ................. | 422/562 |
| 2005/0186113 A1 * | 8/2005 | Koike et al. .................... | 422/63 |
| 2005/0281707 A1 | 12/2005 | Nakaya et al. | |
| 2006/0216199 A1 * | 9/2006 | Koike .............................. | 422/65 |
| 2007/0110617 A1 | 5/2007 | Nagai et al. | |
| 2008/0170967 A1 * | 7/2008 | Itoh ................................ | 422/104 |
| 2008/0190735 A1 * | 8/2008 | Luoma ........................... | 198/340 |

FOREIGN PATENT DOCUMENTS

| | | |
|---|---|---|
| JP | 9-43248 A | 2/1997 |
| JP | 11-295321 A | 10/1999 |

OTHER PUBLICATIONS

Office Action from co-pending U.S. Appl. No. 12/399,498, dated Jul. 20, 2011, 11 pages.

* cited by examiner

*Primary Examiner* — Robert R Raevis
(74) *Attorney, Agent, or Firm* — Brinks Hofer Gilson & Lione

(57) ABSTRACT

An analyzer comprising: a first measurement unit for measuring samples; a second measurement unit; and a transportation device operable to transport a plurality of sample containers accommodated in a first rack and containing samples and a plurality of sample containers accommodated in a second rack and containing samples, to the first measurement unit and the second measurement unit, wherein the transportation device comprises a first transportation section operable to transport the plurality of sample containers on the first rack to the first measurement unit and the second measurement unit by transporting the first rack on a transport path, and a second transportation section operable to transport the plurality of sample containers on the second rack to the first measurement unit and the second measurement unit by transporting the second rack on the transport path independently from movement of the first rack, is disclosed. A transportation device is also disclosed.

10 Claims, 19 Drawing Sheets

ANALYZER AND TRANSPORTATION DEVICE

RELATED APPLICATIONS

This application claims priority under 35 U.S.C. §119 to Japanese Patent Application No. JP2008-057382 filed Mar. 7, 2008, the entire content of which is hereby incorporated by reference.

FIELD OF THE INVENTION

The present invention relates to an analyzer and a transportation device.

BACKGROUND OF THE INVENTION

There has been known an analyzer that automatically transports a plurality of samples and analyzes the transported samples (see U.S. Pat. No. 7,283,217 and US Patent Publication No. 2007-110617). In such an analyzer, one transportation device is connected to one measurement unit.

However, in the analyzer described in U.S. Pat. No. 7,283,217 and US Patent Publication No. 2007-110617, only one measurement unit is provided for one transportation device. Accordingly, it is difficult to largely improve process performance of samples. On the other hand, when such an analyzer is provided with a plurality of measurement units, the process performance of samples is largely improved. However, in that case, a configuration of the transportation device has not been known. For example, to improve the process performance of samples, it is necessary to efficiently transport the samples to the plurality of measurement units. Accordingly, the size of the transportation device increases. When the size of the transportation device is reduced, it is difficult to efficiently transport the samples and thus the process performance of samples deteriorates.

SUMMARY OF THE INVENTION

The scope of the present invention is defined solely by the appended claims, and is not affected to any degree by the statements within this summary.

A first aspect of the present invention is an analyzer for analyzing samples in sample containers accommodated in a rack, the analyzer comprising: a first measurement unit for measuring samples; a second measurement unit for measuring samples; and a transportation device operable to transport a plurality of sample containers accommodated in a first rack and containing samples and a plurality of sample containers accommodated in a second rack and containing samples, to the first measurement unit and the second measurement unit, wherein the transportation device comprises a first transportation section operable to transport the plurality of sample containers on the first rack to the first measurement unit and the second measurement unit by transporting the first rack on a transport path, and a second transportation section operable to transport the plurality of sample containers on the second rack to the first measurement unit and the second measurement unit by transporting the second rack on the transport path independently from movement of the first rack.

A second aspect of the present invention is a transportation device operable to transport a plurality of sample containers accommodated in a first rack and containing samples and a plurality of sample containers accommodated in a second rack and containing samples, to a first measurement unit and a second measurement unit, the transportation device comprising: a first transportation section operable to transport the plurality of sample containers on the first rack to the first measurement unit and the second measurement unit by transporting the first rack on a transportation path; and a second transportation section operable to transport the plurality of sample containers on the second rack to the first measurement unit and the second measurement unit by transporting the second rack on the transport path independently from movement of the first rack.

DETAILED DESCRIPTION OF THE PREFERRED EMBODIMENTS

The preferred embodiments of the present invention will be described hereinafter with reference to the drawings.

Figure 1:
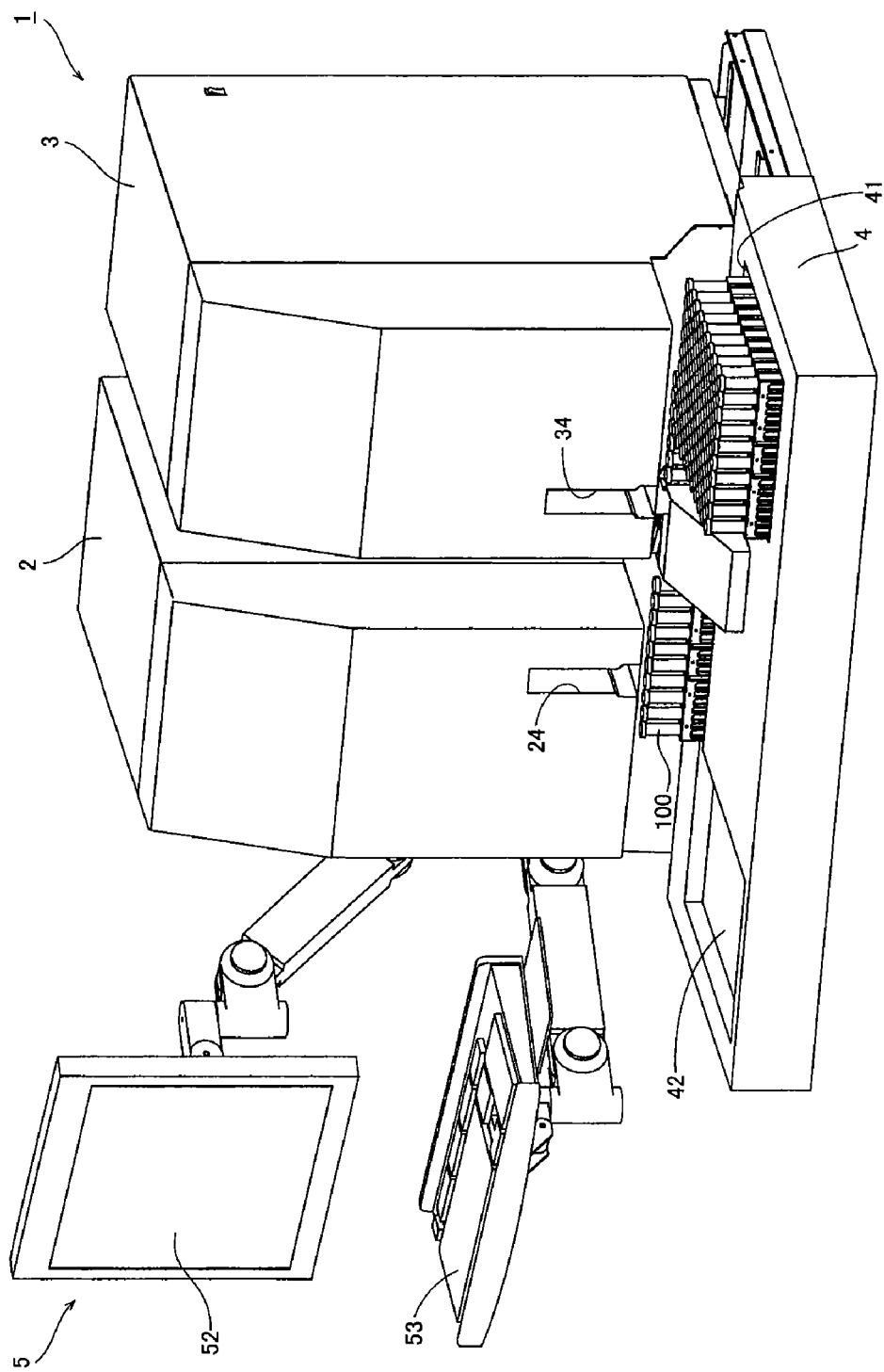
FIG. 1 is a perspective view illustrating an overall configuration of a blood analyzer according to an embodiment of the invention.

FIG. 1 is a perspective view illustrating an overall configuration of a blood analyzer according to an embodiment of the invention. FIG. 2 to FIG. 9 are views for explaining detailed sections of the blood analyzer according to the embodiment shown in FIG. 1. First, the overall configuration of the blood analyzer 1 according to the embodiment of the invention will be described with reference to FIG. 1 to FIG. 9. In the embodiment, the invention is applied to a blood analyzer that is an example of an analyzer.

As shown in FIG. 1, the blood analyzer 1 according to the embodiment of the invention is provided with two measurement units of a first measurement unit 2 and a second measurement unit 3, a sample transportation device (sampler) 4 disposed on the front side of the first measurement unit 2 and the second measurement unit 3, and a control device 5 including a PC (personal computer) electrically connected to the first measurement unit 2, the second measurement unit 3, and the sample transportation device 4. The blood analyzer 1 is connected to a host computer 6 (see FIG. 2) by the control device 5. The first measurement unit 2 and the second measurement unit 3 are the same type of measurement units, and measures samples with respect to the same measurement items using the same measurement principle. The same type includes a case in which a plurality of measurement items of the first measurement unit 2 and a plurality of measurement items of the second measurement unit 3 are partially common, as well as a case in which two measurement units measure samples with respect to the completely same measurement items.

The blood analyzer 1 is not a transportation system in which a plurality of analyzers are connected by the known transportation device but a standalone analyzer. In addition, the blood analyzer 1 may be mounted on the transportation system.

Figure 2:
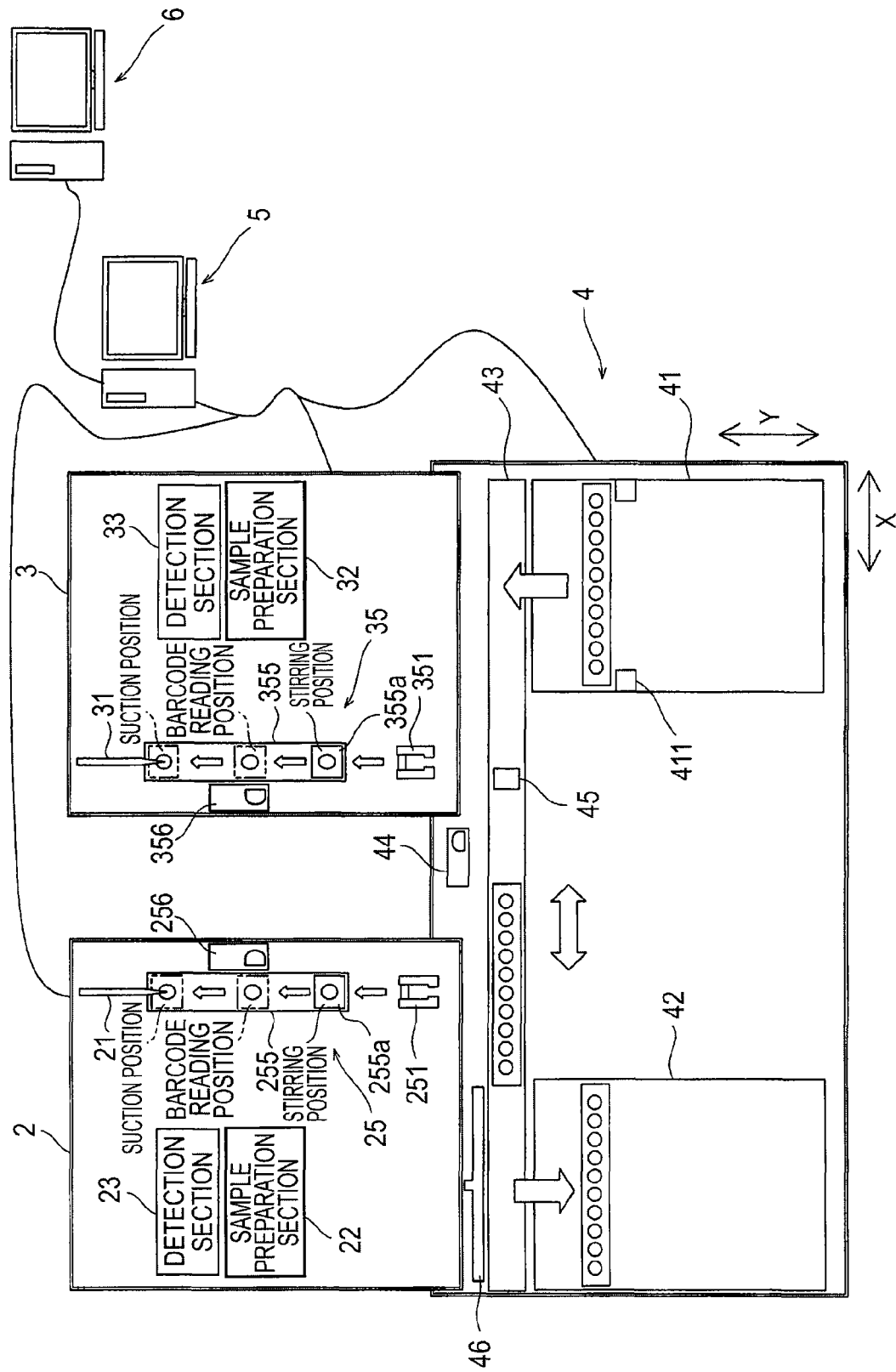
FIG. 2 is a schematic diagram illustrating a measurement unit and a sample transportation device of the blood analyzer according to the embodiment of the invention.
Figure 3:
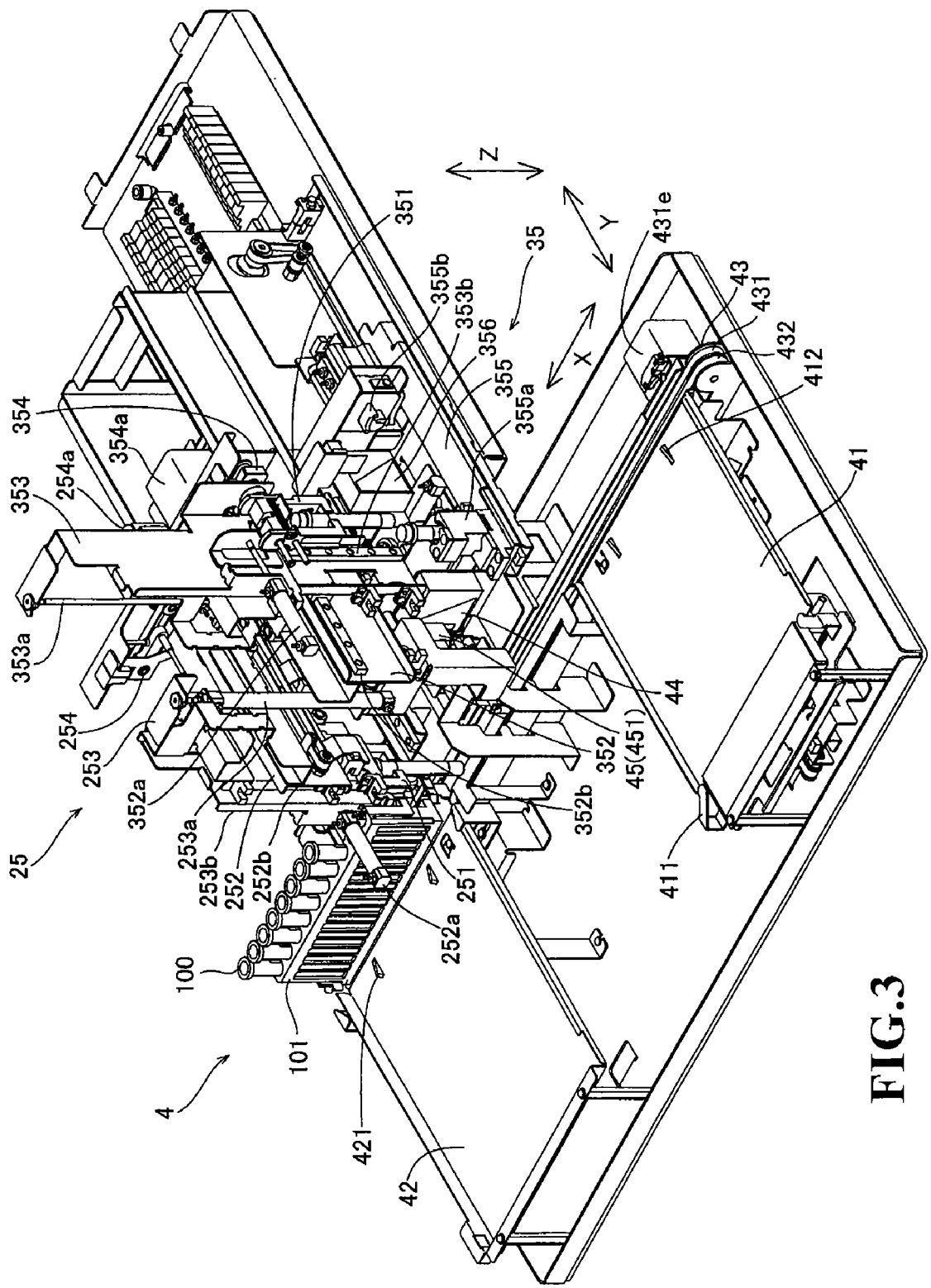
FIG. 3 is a perspective view illustrating a measurement unit and a sample transportation device of the blood analyzer according to the embodiment of the invention.

As shown in FIG. 1 to FIG. 3, the first measurement unit 2 and the second measurement unit 3 are disposed in a mirror shape with is symmetric with respect to a border line between the first measurement unit 2 and the second measurement unit 3. As shown in FIG. 2, the first measurement unit 2 and the second measurement unit 3 include sample suction sections 21 and 31 for sucking blood as a sample from a sample container (test tube) 100, sample preparation sections 22 and 32 for preparing detection samples from the blood sucked by the sample suction sections 21 and 31, and detection sections 23 and 33 for detecting the number of blood cells or hemoglobin from the detection samples prepared by the sample preparation sections 22 and 32, respectively. The first measurement unit 2 and the second measurement unit 3 further include insertion holes 24 and 34 (see FIG. 1) for inserting a sample container 100 accommodated in a rack 101 (see FIG. 4) transported by the sample transportation device 4, and sample container transportation sections 25 and 35 for inserting the sample container 100 from the rack 101 therein and transporting the sample container 100 to a suction position (see FIG. 2) of the sample suction sections 21 and 31, respectively.

Needles (not shown) are provided at the front end portions of the sample suction sections 21 and 31, respectively. The sample suction sections 21 and 31 are configured to move in the vertical direction (direction indicated by the arrow Z), respectively. The sample suction sections 21 and 31 are configured to pass through an airtight cap of the sample container 100 transported to the suction position by moving downward and to suck inner blood.

The detection sections 23 and 33 are configured to perform RBC detection (detection of the number of red blood cells) and PLT detection (detection of the number of platelets) by a sheath flow DC detection method and to perform HGB detection (detection of the amount of hemoglobin in blood) by an SLS-hemoglobin method. The detection sections 23 and 33 are configured to perform WBC detection (detection of the number of white blood cells) by a flow cytometry method using semiconductor laser.

The detection result obtained by the detection sections 23 and 33 are transmitted to the control device 5, as measurement data (measurement result) of samples. The measurement data is a basis of a final analysis result (the number of red blood cells, the number of platelets, the amount of hemoglobin, the number of white blood cells, etc.) provided for a user.

As shown in FIG. 3, the sample container transportation sections 25 and 35 has hand sections 251 and 351 for gripping the sample container 100, horizontal moving sections 252 and 352 for horizontally and straightly moving the hand sections 251 and 351 in the direction indicated by the arrow Y, vertical moving sections 253 and 353 for straightly moving the hand sections 251 and 351 in the vertical direction (direction indicated by the arrow Z), and stirring sections 254 and 354 for moving the hand sections 251 and 351 in a pendulum shape in the vertical direction (direction indicated by the arrow Z), respectively. The sample container transportation sections 25 and 35 further have sample container moving sections 255 and 355 for holding the sample container 100 acquired from the rack 101 by the hand sections 251 and 351 to sample set sections 255a and 355a, and for horizontally and straightly moving in the direction indicated by the arrow Y to the suction position of the sample suction sections 21 and 31, and barcode reading sections 256 and 356, respectively.

The hand sections 251 and 351 move in the horizontal direction (direction indicated by the arrow Y) to move to the upper part of the sample container 100 accommodated in the rack 101 transported by the sample transportation device 4, and then move in the vertical direction (direction indicated by the arrow Z) to grip the sample container 100 placed at the lower part thereof. The hand sections 251 and 351 move the gripped sample container 100 to the upper part to extract the gripped sample container 100 from the rack 101, and move in the horizontal direction (direction indicated by the arrow Y) to a stirring position (see FIG. 2). At the stirring position, the hand sections 251 and 351 move (e.g., 10 times reciprocation) in the pendulum shape by the stirring sections 254 and 354, thereby stirring blood in the gripped sample container 100. After finishing the stirring, the hand sections 251 and 351 move downward to set the sample container 100 at the sample set sections 255a and 355a of the sample container moving sections 255 and 355 and release the gripping.

The horizontal moving sections 252 and 352 are configured to move the hand sections 251 and 351 in the horizontal direction (direction indicated by the arrow Y) along rails 252b and 352b by power of air cylinders 252a and 352a, respectively.

The vertical moving sections 253 and 353 are configured to move the hand sections 251 and 351 in the vertical direction (direction indicated by the arrow Z) along the rails 253b and 353b by power of the air cylinders 253a and 353a, respectively.

The stirring sections 254 and 354 are configured to move the hand sections 251 and 351 in a pendulum shape in the vertical direction (direction indicated by the arrow Z) by power of stepping motors 254a and 354a, respectively.

The sample container moving sections 255 and 355 are configured to transport the sample set sections 255a and 355a to suction positions in the direction indicated by the arrow Y by power of stepping motors (not shown), and to bring the sample container 100 accommodated in the sample set sections 255a and 355a into contact with a restriction section 355b (restriction section on the first measurement unit 2 side is not shown), respectively. With such a configuration, the sample container 100 is clamped (fixed) at each suction position. It is possible to suck a sample from the sample container 100 by moving the sample container moving sections 255 and 355 to the suction positions as the sample container 100 is viewed in a plan view, only by moving in the vertical direction (direction indicated by the arrow Z), without moving the sample suction sections 21 and 31 in the horizontal direction (direction indicated by the arrows X and Y).

Figure 4:
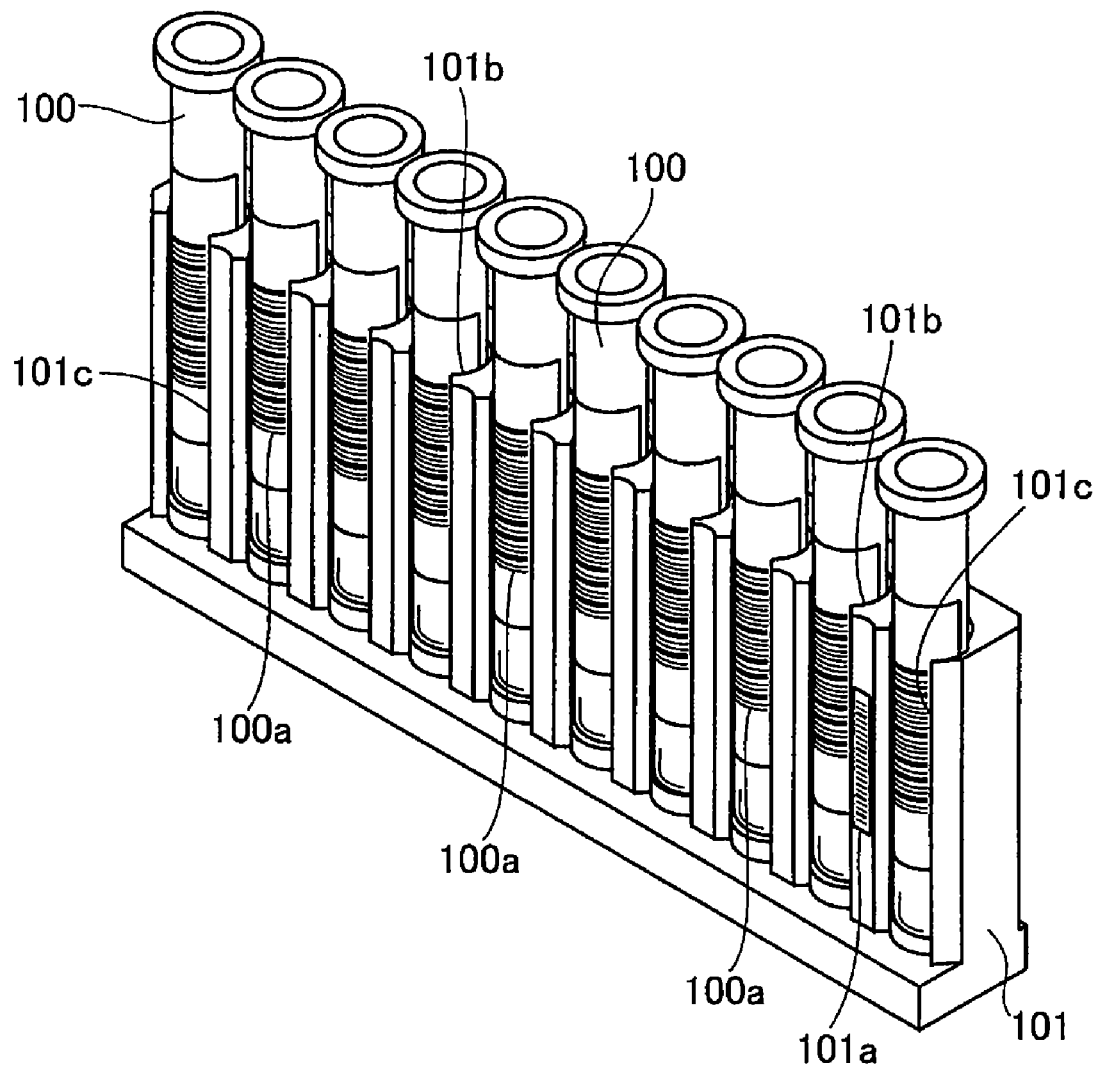
FIG. 4 is a perspective view illustrating a rack and sample containers of the blood analyzer according to the embodiment of the invention.

The barcode reading sections 256 and 356 are configured to read a barcode 100a attached to each sample container 100 as shown in FIG. 4. The barcode reading sections 256 and 356 are configured to read the barcode 100a of the sample container 100 while rotating in the horizontal direction with the sample container 100 as a target set at the sample set sections 255a and 355a by a rotation device (not shown). Accordingly, even when the barcode 100a of the sample container 100 is attached to the opposite side to the barcode reading sections 256 and 356, it is possible to turn the barcode 100a toward the barcode reading sections 256 and 356 by rotating the sample container 100. Each barcode 100a of each sample container 100 is uniquely attached to each sample, and is used to manage the analysis result of each sample.

Figure 5:
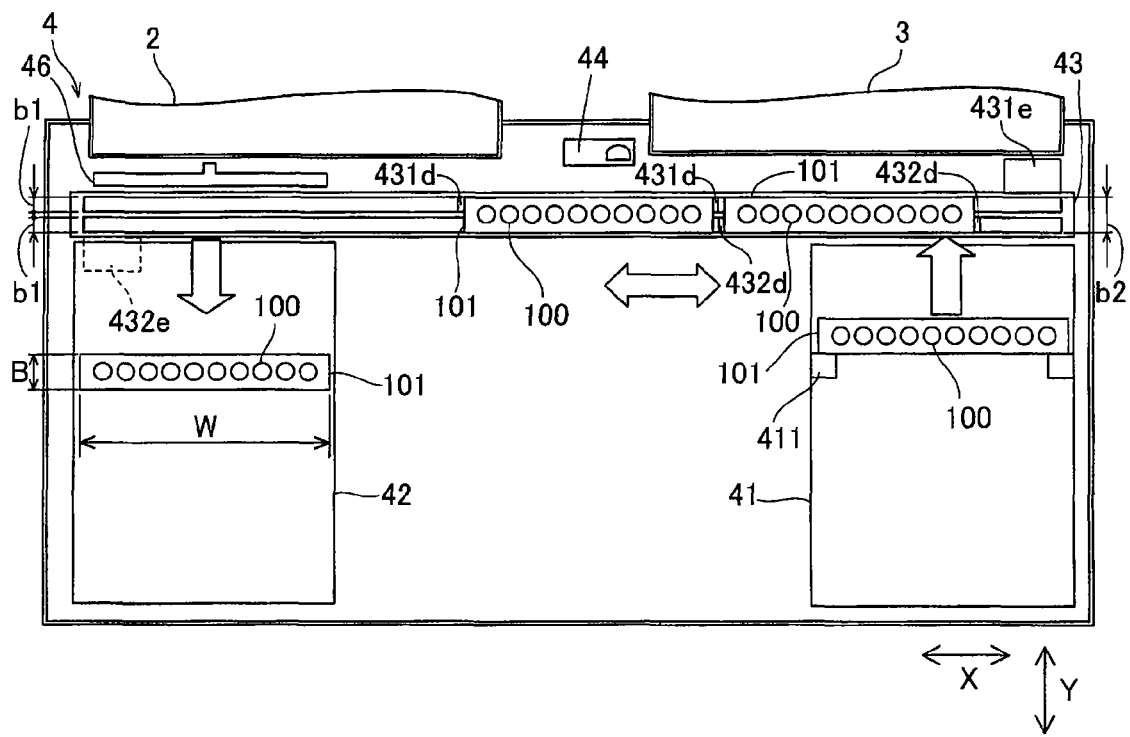
FIG. 5 is a plan view for explaining the sample transportation device of the blood analyzer according to the embodiment of the invention.
Figure 6:
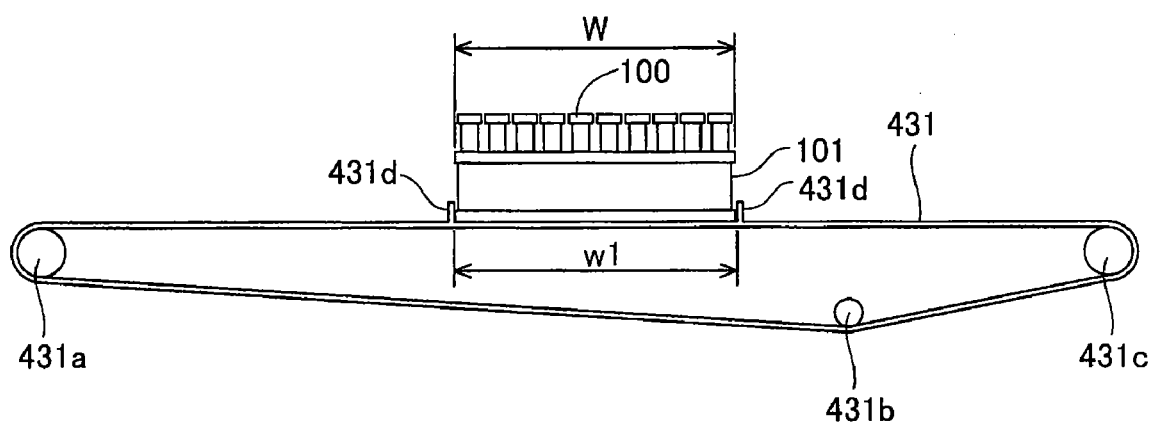
FIG. 6 is a side view for explaining the sample transportation device of the blood analyzer according to the embodiment of the invention.
Figure 7:
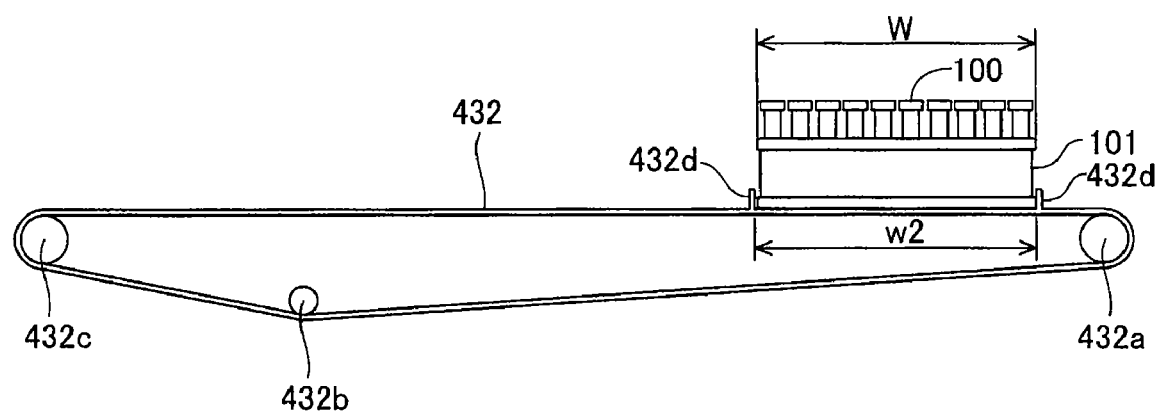
FIG. 7 is a side view for explaining the sample transportation device of the blood analyzer according to the embodiment of the invention.

In the embodiment, as shown in FIG. 3 and FIG. 5, the sample transportation device 4 includes a before-analysis rack holding section 41 capable of holding the plurality of racks 101 accommodating the sample containers 100 for accommodating samples before performing analysis, an after-analysis rack holding section 42 capable of holding the plurality of racks 101 accommodating the sample containers 100 for accommodating the samples after performing analysis, a rack transportation section 43 for horizontally and straightly moving the rack 101 in the direction indicated by the arrow X, a barcode reading section 44, a presence sensing sensor 45 for sensing whether or not there is the sample container 100, and a rack output section 46 for moving the rack 101 into the after-analysis rack holding section 42.

The before-analysis rack holding section 41 having a rack input section 411 is configured to output the rack 101 held to the before-analysis rack holding section 41 one by one onto the rack transportation section 43 by moving the rack input section 411 in the direction indicated by the arrow Y. The rack input section 411 is configured to be driven by a stepping motor (not shown) provided below the before-analysis rack holding section 41. The before-analysis rack holding section 41 having a restriction section 412 (see FIG. 3) in the vicinity of the rack transportation section 43 is configured to restrict movement of the rack 101 so that the rack 101 output onto the rack transportation section 43 once does not return into the before-analysis rack holding section 41.

The after-analysis rack holding section 42 having a restriction section 421 (FIG. 3) in the vicinity of the rack transportation section 43 is configured to restrict movement of the rack 101 so that the rack 101 moved into the after-analysis rack holding section 42 once does not return to the rack transportation section 43.

The rack transportation section 43 has two belts of a first belt 431 and a second belt 432 capable of transporting the rack 101 independently from each other. As shown in FIG. 5, the first belt 431 and the second belt 432 are disposed adjacent and parallel to each other in the direction (direction indicated by the arrow Y) perpendicular to the transportation direction (direction indicated by the arrow X), so that the placed racks 101 are placed on both sides of the first belt 431 and the second belt 432 in the plan view. Accordingly, the rack 101 is transported in the direction (direction indicated by the arrow X) substantially parallel to a straight line connecting the front of the first measurement unit 2 and the front of the second measurement unit 3. Each of widths b1 and b2 (see FIG. 5) of the first belt 431 and the second belt 432 in the direction indicated by the arrow Y is half of or less than half of a width B of the rack 101 in the direction indicated by the arrow Y. Accordingly, a total width b2 of the first belt 431 and the second belt 432 can be set as a width allowing only one rack 101 to pass. In addition, a width of the transportation path of the rack 101 is the width allowing only one rack 101 to pass. The first belt 431 and the second belt 432 have a ring shape, and are disposed to surround rollers 431a to 431c (see FIG. 6) and rollers 432a to 432c (see FIG. 7), respectively. Two protrusion pieces 431d are formed at outer peripheral section of the first belt 431 to have an inner width w1 (see FIG. 6) slightly (e.g., about 1 mm) larger than the width W of the rack 101 in the direction indicated by the arrow X. Two protrusion pieces 432d are formed at output peripheral sections of the second belt 432 to have an inner width w2 (see FIG. 7) slightly (e.g., about 1 mm) larger than the width W of the rack 101 in the direction indicated by the arrow X. The rack 101 is input from the before-analysis rack holding section 41 to a space between the two protrusion pieces 431d of the first belt 431 or to a space between the two protrusion pieces 432d of the second belt 432.

Figure 8:
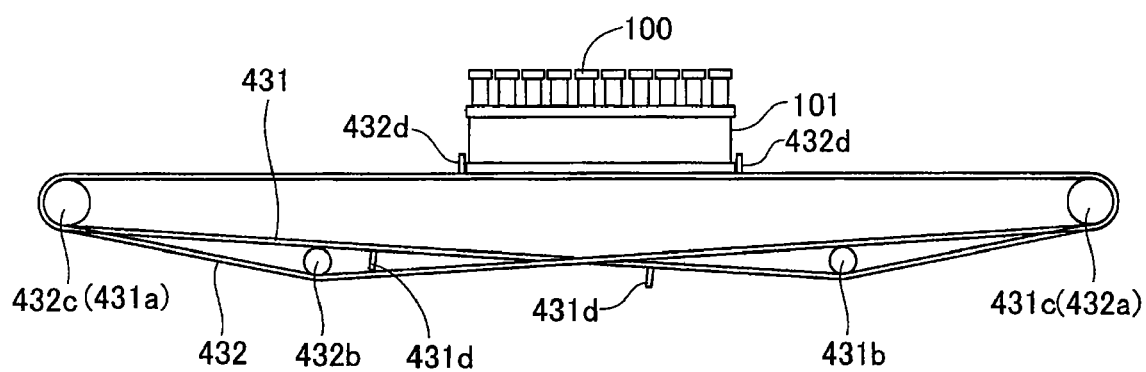
FIG. 8 is a side view for explaining the sample transportation device of the blood analyzer according to the embodiment of the invention.

The first belt 431 move along the outer peripheries of the rollers 431a to 431c by the stepping motor 431e (see FIG. 3 and FIG. 5) with the rack 101 kept inside the protrusion pieces 431d, thereby moving the rack 101 in the direction indicated by the arrow X. Specifically, the rack 101 comes into contact with the protrusion piece 431d disposed on the rear side of the belt with respect to the moving direction of the first belt 431, thereby pushing the rack 101 to move in the moving direction of the first belt 431. Although the bottom of the rack 101 comes into contact with an outer peripheral surface of the other second belt 432 when the rack 101 moves, friction force between the bottom of the rack 101 and the outer peripheral surface of the second belt 432 is very smaller than pressing force in the moving direction of the rack 101 by the protrusion piece 431d. For this reason, the first belt 431 can independently move the rack 101 irrespective of the movement of the second belt 432. As shown in FIG. 8, two protrusion pieces 431d of the first belt 431 is configured to move by passing through the downside of the first belt 431 from the rack output position where the rack 101 is moved from the transportation path into the after-analysis rack holding section 42, to the rack input position where the rack 101 is input from the inside of the before-analysis rack holding section 41 to the transportation path. The second belt 432 is configured the same as the first belt 431, and is moved by the stepping motor 432e (see FIG. 5).

The barcode reading section 44 is configured to read the barcode 100a of the sample container 100 shown in FIG. 4 and to read the barcode 101a attached to the rack 101. The barcode reading section 44 is configured to read the barcode 100a of the sample container 100 while rotating in the horizontal direction with the sample container 100 as a target accommodated in the rack 101 by a rotation device (not shown). Accordingly, even when the barcode 100a of the sample container 100 is attached to the opposite side to the barcode reading section 44, it is possible to turn the barcode 100a toward the barcode reading section 44 by rotating the sample container 100. The barcode 101a of the rack 101 is uniquely attached to each rack, and is used to manage the analysis result of each sample.

The presence sensing sensor 45 is a contact type sensor, and has a contact piece 451 (see FIG. 3) having a curtain shape, a light emitting element (not shown) emitting light, and a light receiving element (not shown). The presence sensing sensor 45 is configured so that the contact piece 451 is bent when the contact piece 451 comes into contact with a sensing object that is a sensing target, and thus light emitted from the light emitting element is reflected to the contact piece 451, and the reflected light enters the light receiving element. Accordingly, when the sample container 100 that is a sensing target accommodated in the rack 101 passes through the downside of the presence sensing sensor 45, the contact piece 451 is bent by the sample container 100, thereby sensing that there is the sample container 100.

The rack output section 46 is opposed to the after-analysis rack holding section 42 with the rack transportation section 43 interposed therebetween, and is configured to horizontally and straightly move in the direction indicated by the arrow Y. Accordingly, when the rack 101 is transported to a position (hereinafter, referred to as a rack output position) between the after-analysis rack holding section 42 and the rack output section 46, the rack output section 46 is moved to the after-analysis rack holding section 42, thereby pressing the rack 101. Therefore, it is possible for the rack 101 to move into the after-analysis rack holding section 42.

Figure 9:
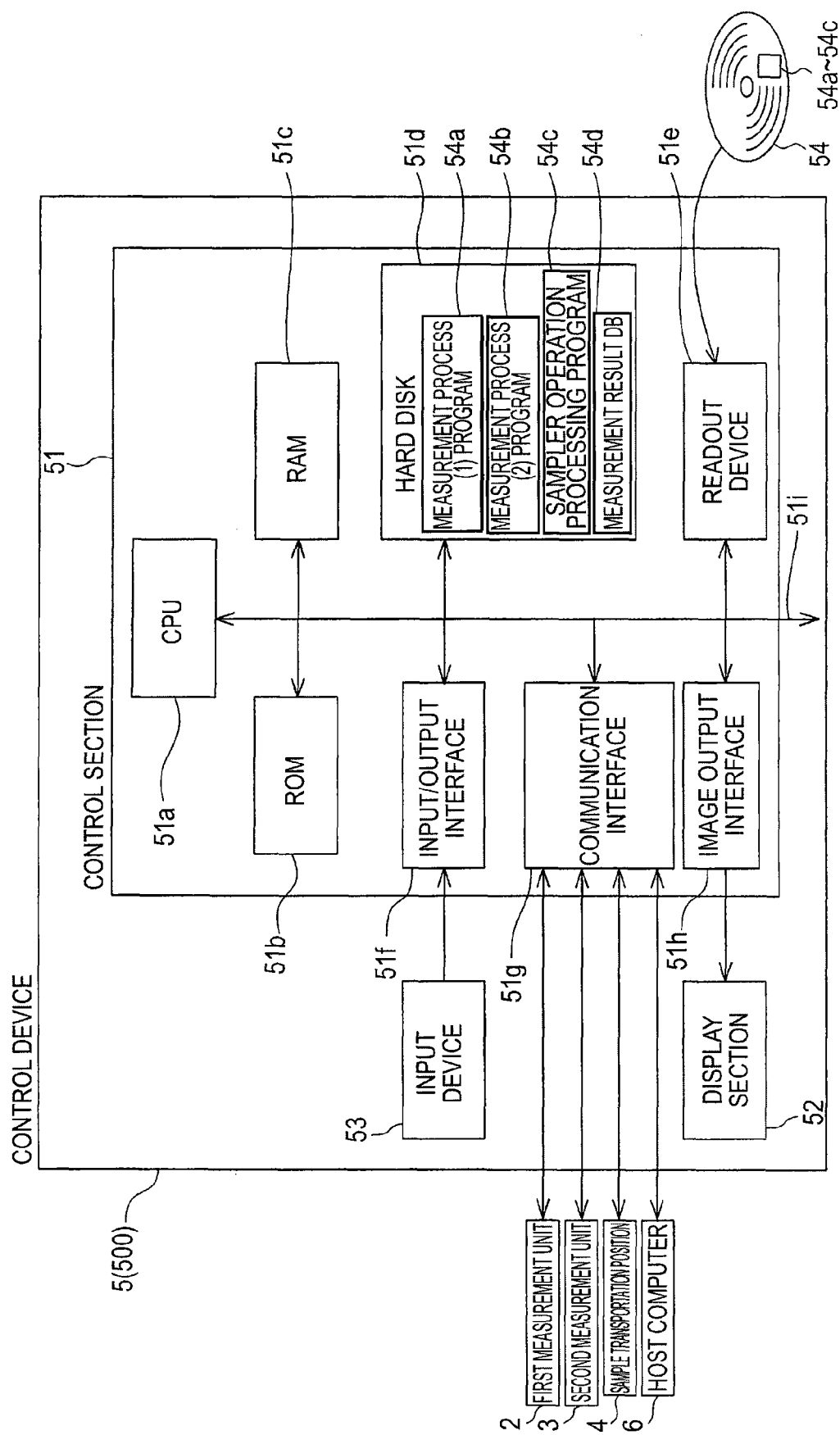
FIG. 9 is a block diagram for explaining a control device of the blood analyzer according to the embodiment of the invention.

As shown in FIG. 1 and FIG. 9, the control device 5 is configured of a personal computer (PC) or the like, and includes a control unit 51 configured of a CPU, a ROM, a RAM, and the like, a display unit 52, and an input device 53. The display unit 52 is provided to display analysis results and the like obtained by analyzing data of digital signals transmitted from the first measurement unit 2 and the second measurement unit 3.

Next, a configuration of the control device 5 will be described. As shown in FIG. 9, the control device 5 is configured of a computer 500 mainly including a control unit 51, a display unit 52, and an input device 53. The control unit 51 mainly includes a CPU 51a, a ROM 51b, a RAM 51c, a hard disk 51d, a readout device 51e, an input/output interface 51f, a communication interface 51g, and an image output interface 51h. The CPU 51a, the ROM 51b, the RAM 51c, the hard disk 51d, the readout device 51e, the input/output interface 51f, the communication interface 51g, and the image output interface 51h are connected by a bus 51i.

The CPU 51a can execute a computer program stored in the ROM 51b and a computer program loaded on the RAM 51c. The CPU 51a executes application programs 54a to 54c, whereby the computer 500 functions as the control device 5.

The ROM 51b is configured of a mask ROM, a PROM, an EPROM, an EEPROM, or the like, in which computer programs executed by the CPU 51a and data used for the computer programs are recorded.

The RAM 51c is configured of an SRAM, a DRAM, or the like. The RAM 51c is used to read the computer programs recorded in the ROM 51b and the hard disk 51d. The RAM 51c is used as a work area of the CPU 51a when the computer programs are executed.

In the hard disk 51d, various computer programs such as an operating system and application programs executed by the CPU 51a, and data used for executing the computer programs are installed. A measurement processing program 54a for the first measurement unit 2, a measurement processing program 54b for the second measurement unit 3, and a measurement processing program 54c for the sample transportation device 4 are also installed in the hard disk 51d. The application programs 54a to 54c are executed by the CPU 51a, thereby controlling an operation of each section of the first measurement unit 2, the second measurement unit 3, and the sample transportation device 4. A measurement result database 54d is also installed therein.

The readout device 51e is configured of a flexible disk drive, a CD-ROM drive, a DVD-ROM drive, or the like, and can read computer programs or data recorded in a transportable recording medium 54. The application programs 54a to 54c are stored in the transportable recording medium 54, the computer 500 reads the application programs 54a to 54c from the transportable recording medium 54, and the application programs 54a to 54c can be installed in the hard disk 51d.

The application programs 54a to 54c are not only provided by the transportable recording medium 54 but may be provided from an external device connected to communicate with the computer 500 by an electric communication line (irrespective of wire and wireless) through the electric communication line. For example, the application programs 54a to 54c are stored in a hard disk of a server computer on the Internet, the computer 500 accesses to the server computer, the application programs 54a to 54c are downloaded, and the application programs 54a to 54c are installed in the hard disk 51d.

An operating system providing graphical user interface environment such as Windows (trade mark) produced by Microsoft Inc. in USA is installed in the hard disk 51d. In the following description, it is assumed that the application programs 54a to 54c are operated on the operating system.

The input/output interface 51 f is configured of, for example, a serial interface such as USB, IEEE1394, and RS-232C, a parallel interface such as SCSI, IDE, and IEEE1284, an analog interface including a D/A converter and A/D converter, and the like. The input device 53 is connected to the input/output interface 51f, and a user uses the input device 53, thereby inputting data to the computer 500.

The communication interface 51g is, for example, an Ethernet (trade mark) interface. The computer 500 can transmit and receive data among the first measurement unit 2, the second measurement unit 3, the sample transportation device 4, and the host computer 6 using a predetermined communication protocol by the communication interface 51g.

The image output interface 51h is connected to the display unit 52 configured of LCD, CRT, or the like, and displays video signals based on the image data given from the CPU 51a on the display unit 52. The display unit 52 displays images (screen) according to the input video signals.

With such a configuration, the control unit 51 is configured to analyze components of an analysis target using the measurement result transmitted from the first measurement unit 2 and the second measurement unit 3, and to acquire the analysis result (the number of red blood cells, the number of platelets, the amount of hemoglobin, the number of white blood cells, etc.).

As shown in FIG. 4, ten container accommodating sections 101*b* are formed in the rack 101 to accommodate ten sample containers 100 in series. The container accommodating sections 101*b* are provided with opening sections 101*c* so that the barcode 100*a* of each accommodated sample container 100 is visible.

Figure 10:
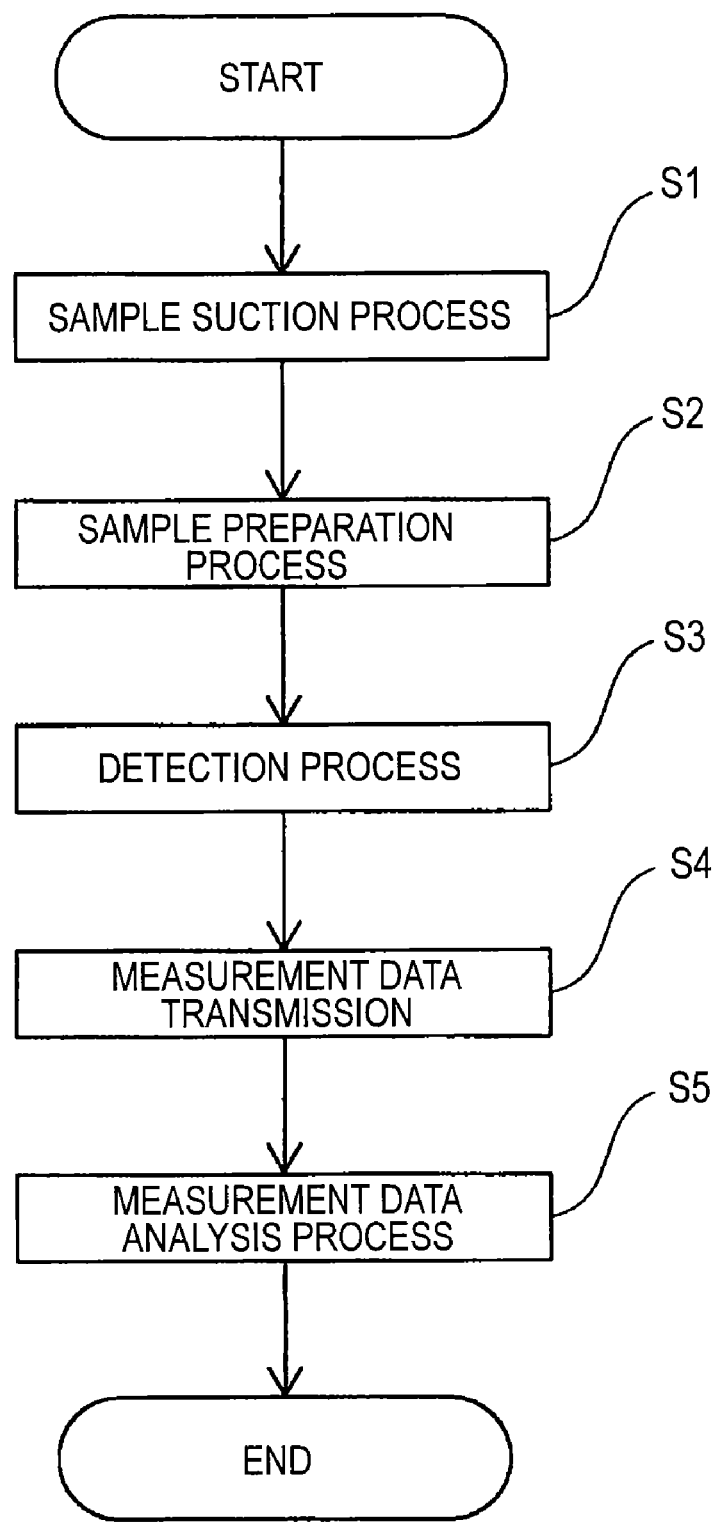
FIG. 10 is a flowchart for explaining a measurement processing operation performed by a measurement processing program of the blood analyzer according to the embodiment of the invention.
Figure 11:
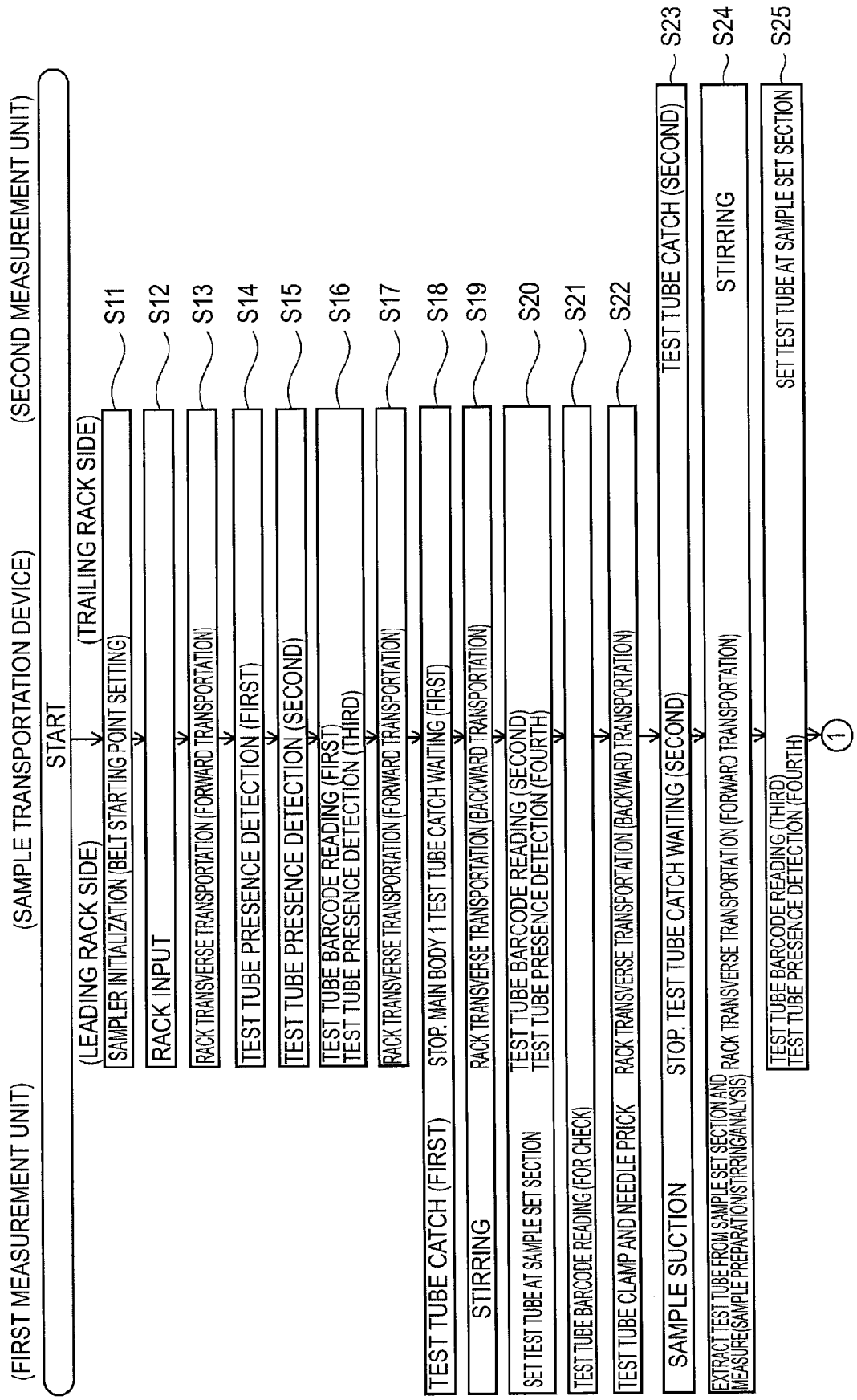
FIG. 11 is a flowchart for explaining the contents of a measurement processing (1) program 54a, a measurement processing (2) program 54b, and a sampler operation processing program 54c.
Figure 12:
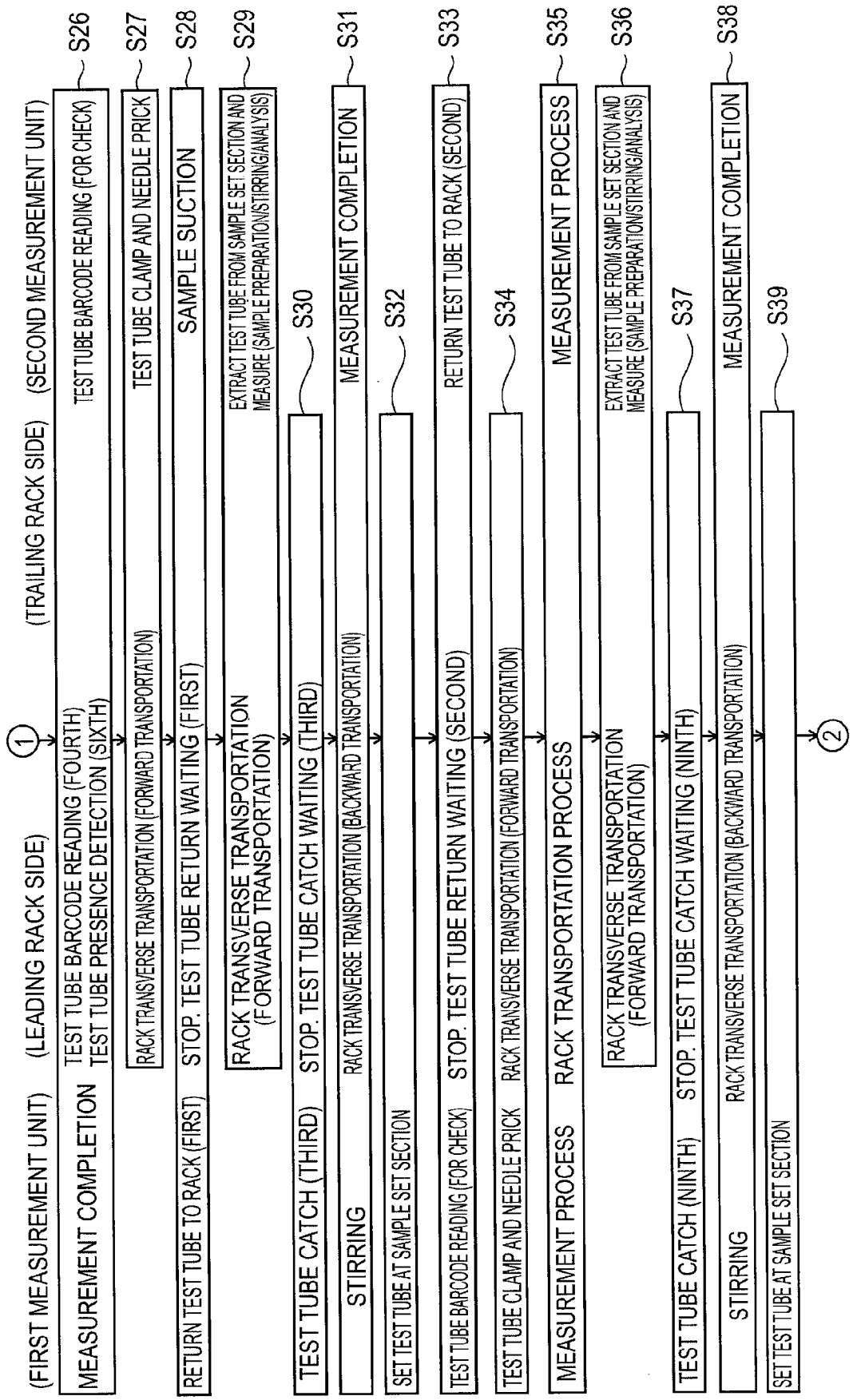
FIG. 12 is a flowchart for explaining the contents of a measurement processing (1) program 54a, a measurement processing (2) program 54b, and a sampler operation processing program 54c.
Figure 13:
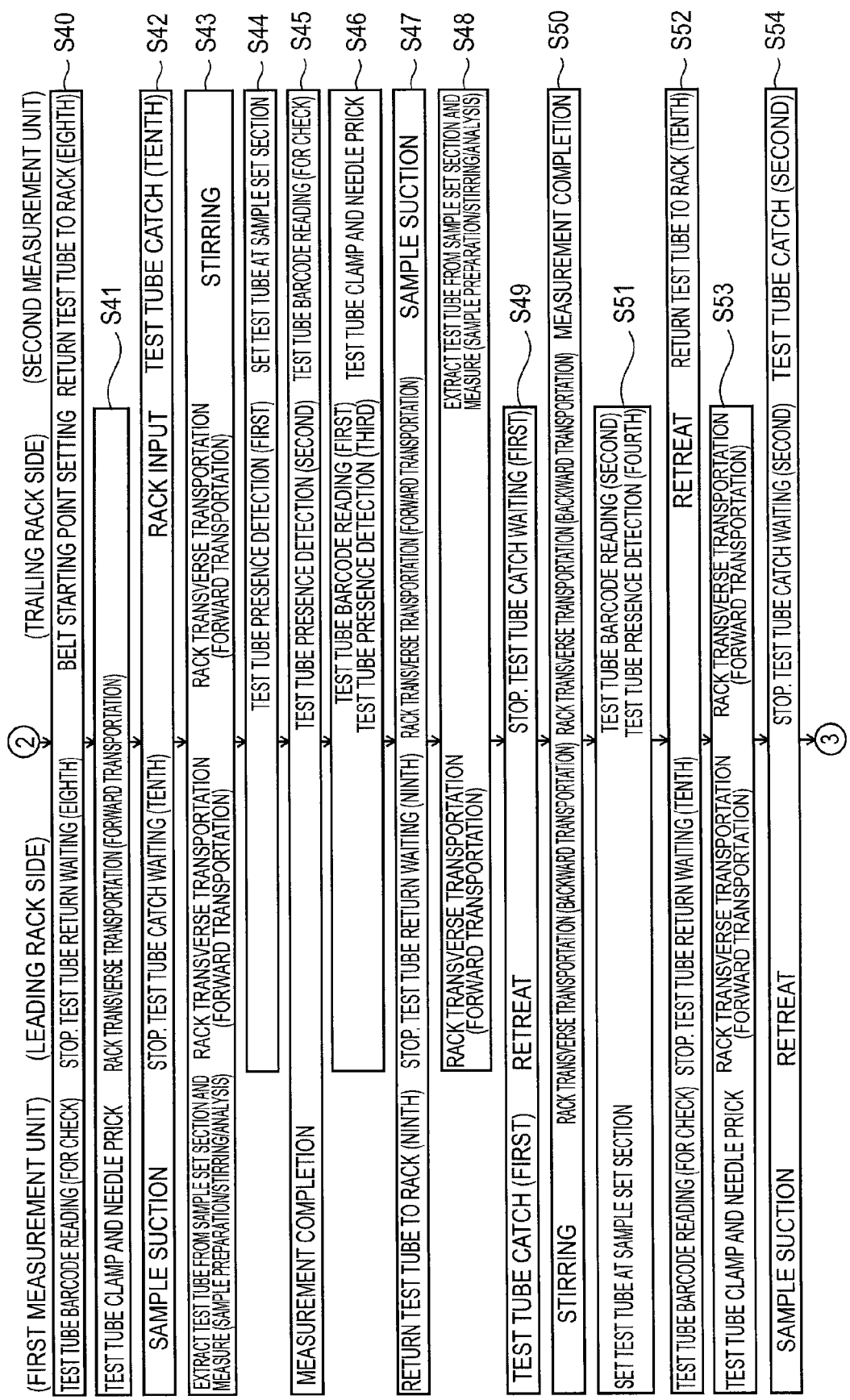
FIG. 13 is a flowchart for explaining the contents of a measurement processing (1) program 54a, a measurement processing (2) program 54b, and a sampler operation processing program 54c.
Figure 14:
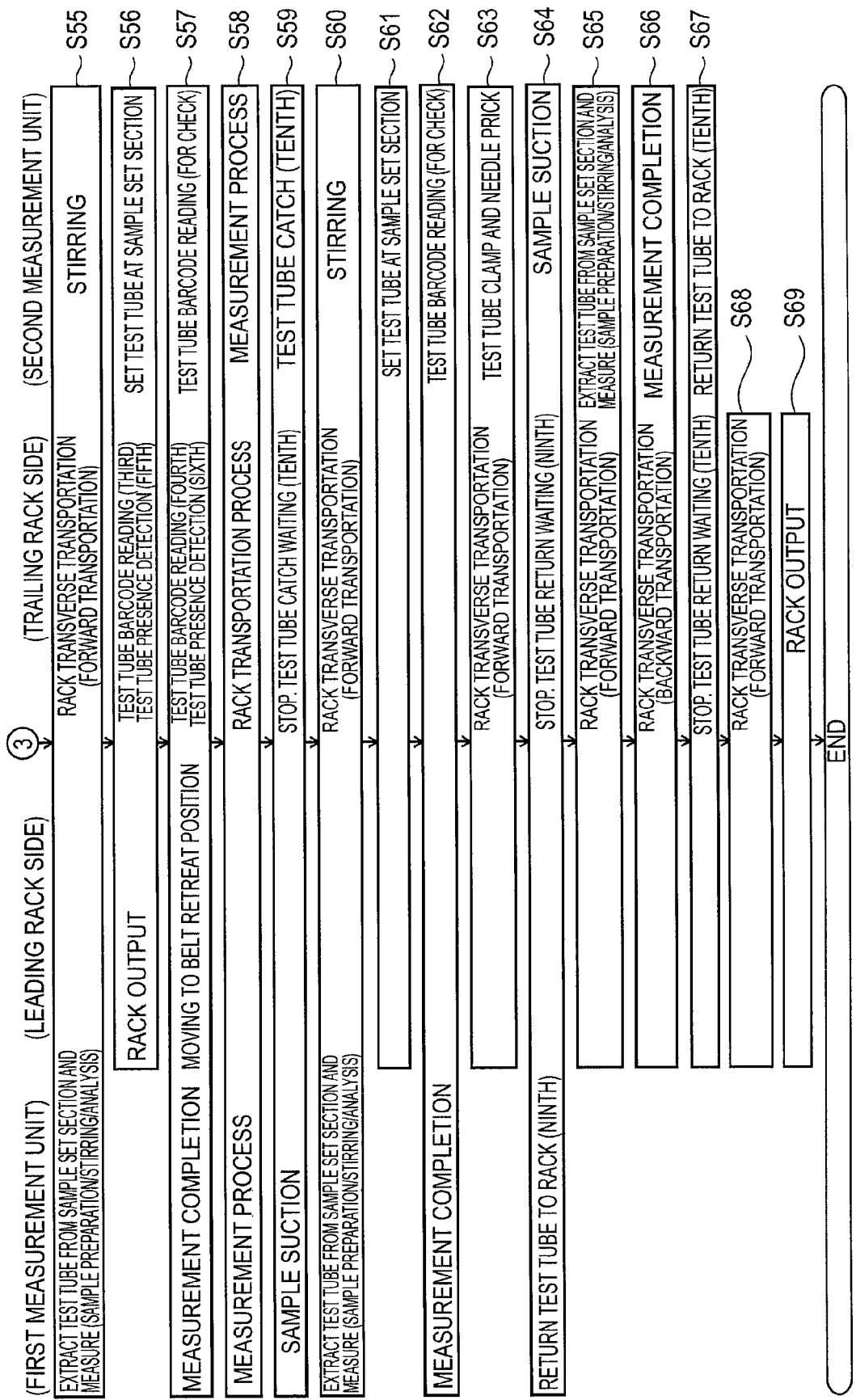
FIG. 14 is a flowchart for explaining the contents of a measurement processing (1) program 54a, a measurement processing (2) program 54b, and a sampler operation processing program 54c.

FIG. 10 is a flowchart for explaining measurement processing operations by the measurement processing programs of the blood analyzer according to the embodiment of the invention. Next, the measurement processing operations by the measurement processing programs 54*a* and 54*b* of the blood analyzer 1 according to the embodiment will be described with reference to FIG. 10. The components of the analysis target are measured in the first measurement unit 2 and the second measurement unit 3 in the same manner. Accordingly, the case where the components of the analysis target are measured by the first measurement unit 2 will be described herein as a representative example.

First, in Step S1, suction of samples is performed from the transported sample container 100 to the suction position (see FIG. 2) by the sample suction section 21. In Step S2, a detection sample is prepared from the sucked sample by the sample preparation section 22. In Step S3, components of the analysis target are detected from the detection sample by the detection section 23. In Step S4, measurement data is transmitted from the first measurement unit 2 to the control device 5. In Step S5, the components of the analysis target are analyzed by the control unit 51 on the basis of the measurement result transmitted from the first measurement unit 2. The analysis of the sample is completed by Step S5, and the operation is completed.

Figure 15:
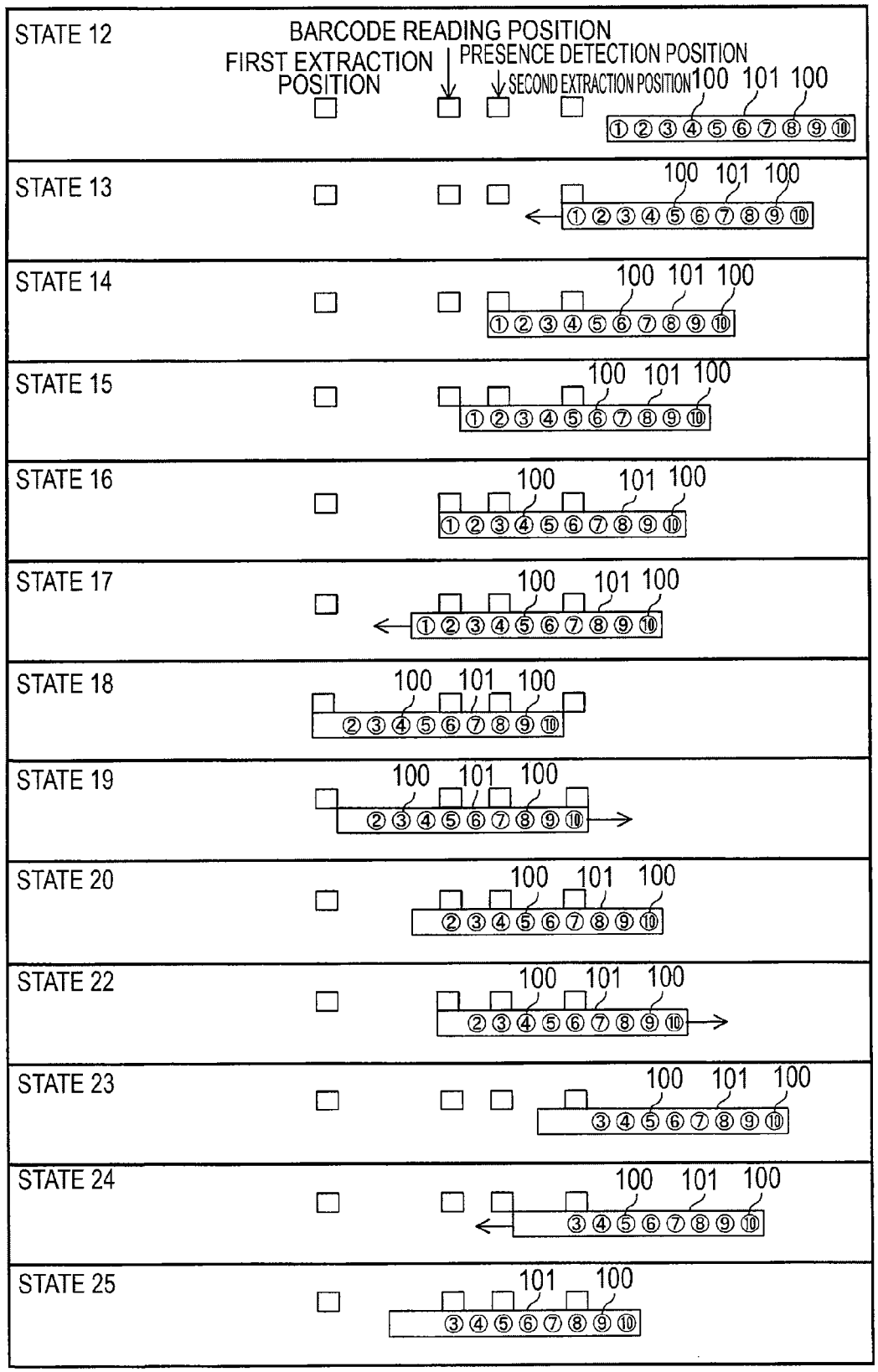
FIG. 15 is a diagram illustrating a positional relationship of each section and the rack and sample containers of the blood analyzer according to the embodiment of the invention.
Figure 16:
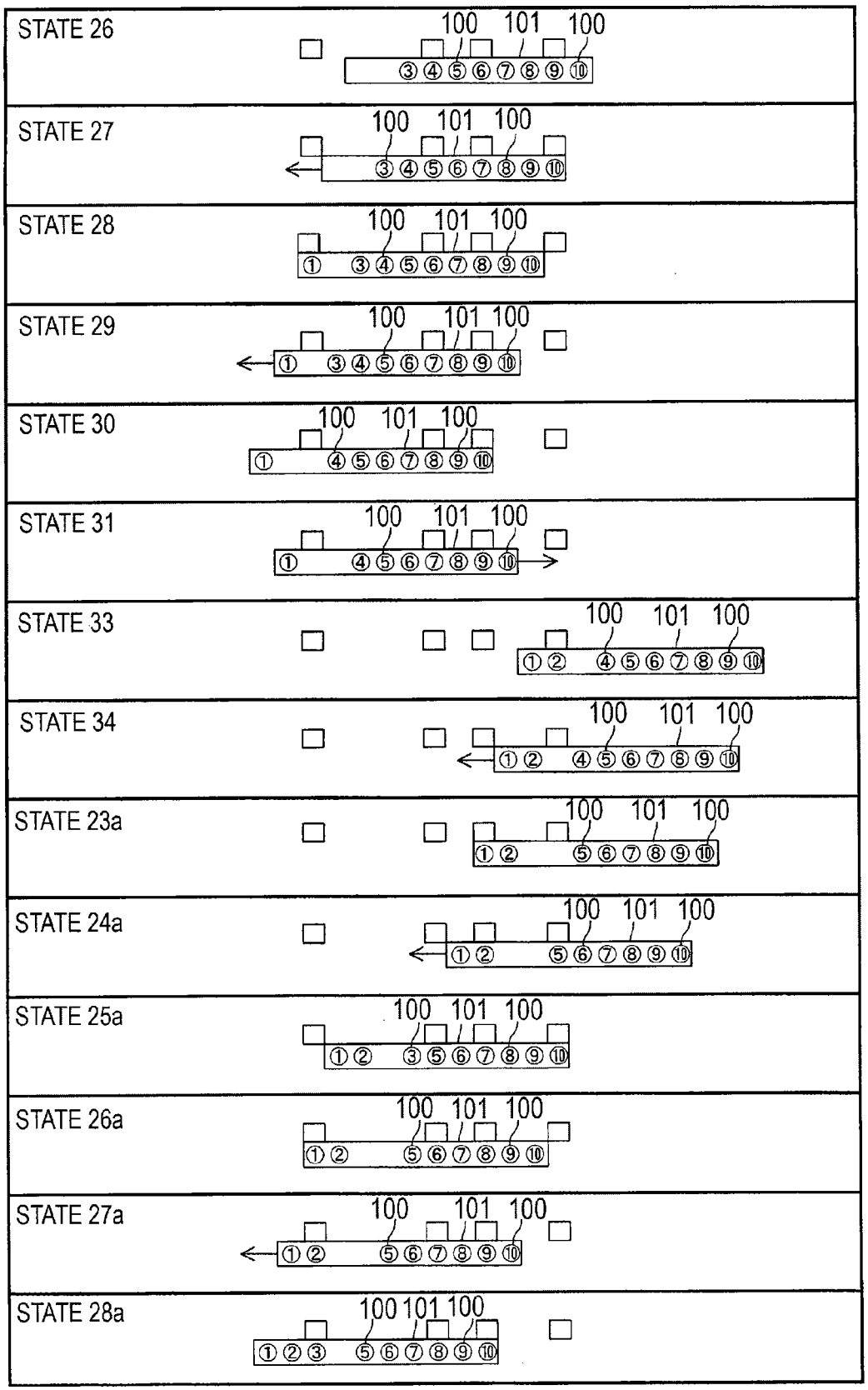
FIG. 16 is a diagram illustrating a positional relationship of each section and the rack and sample containers of the blood analyzer according to the embodiment of the invention.
Figure 17:
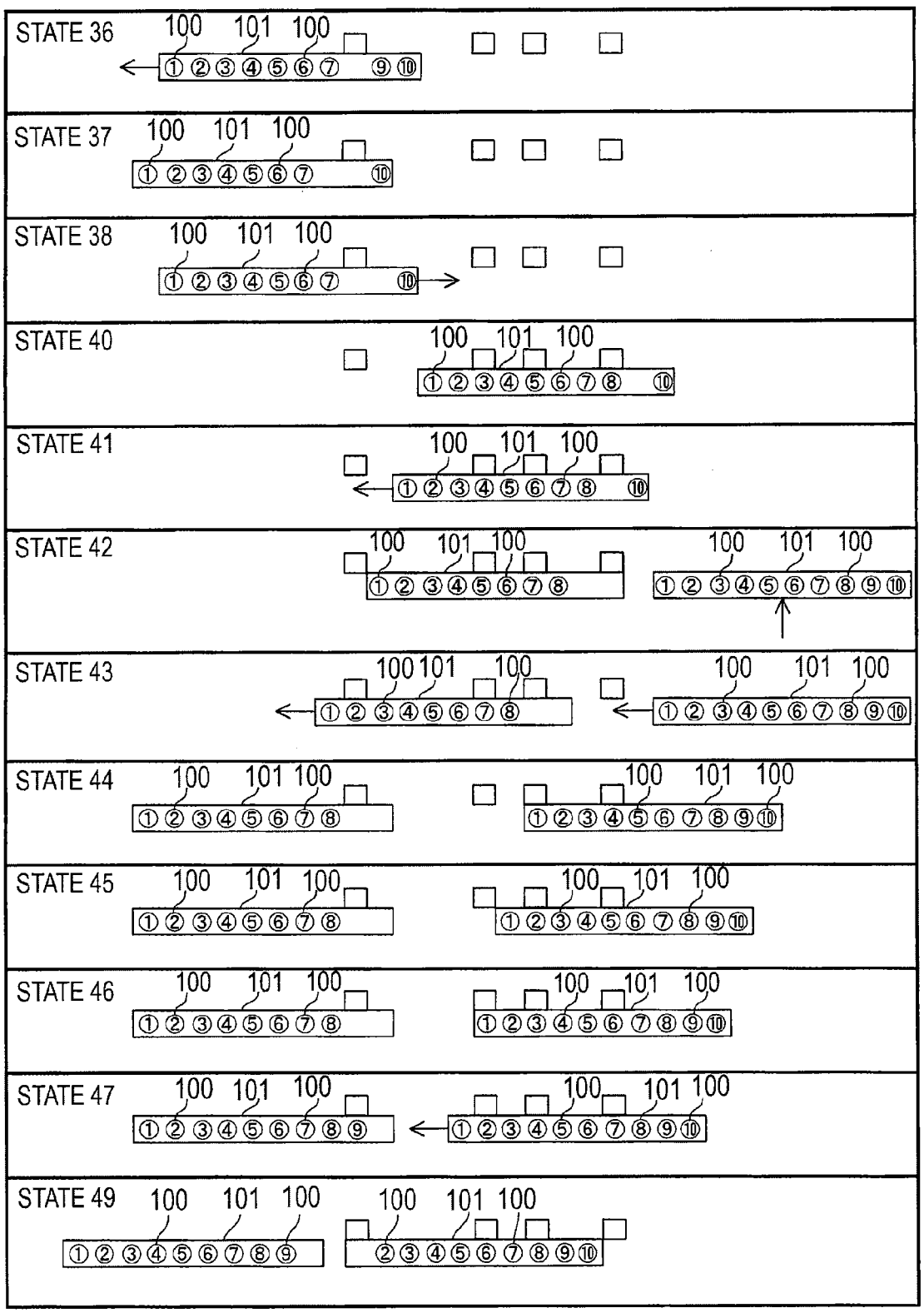
FIG. 17 is a diagram illustrating a positional relationship of each section and the rack and sample containers of the blood analyzer according to the embodiment of the invention.
Figure 18:
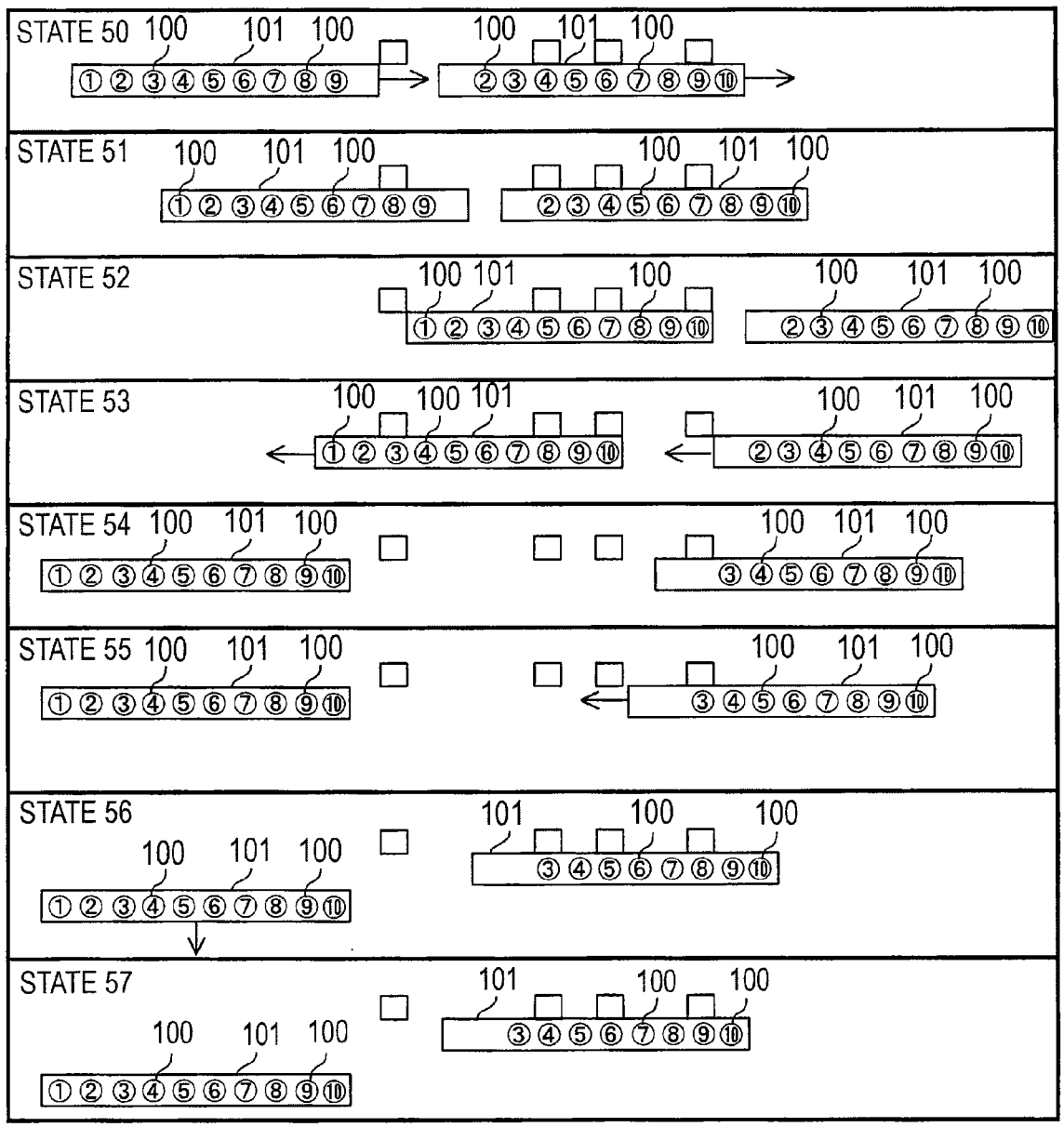
FIG. 18 is a diagram illustrating a positional relationship of each section and the rack and sample containers of the blood analyzer according to the embodiment of the invention.

FIG. 11 to FIG. 14 are flowcharts for explaining the contents of a measurement processing (1) program 54*a*, a measurement processing (2) program 54*b*, and a sampler operation processing program 54*c*. FIG. 15 to FIG. 18 are diagrams illustrating positional relationships of the rack, the sample containers, and the sections of the blood analyzer according to the embodiment of the invention. Next, a series of operations of the first measurement unit 2, the second measurement unit 3, and the sample transportation device 4 of the blood analyzer 1 according to the embodiment will be described with reference to FIG. 11 to FIG. 18. In the flowcharts shown in FIG. 11 to FIG. 14, the content of the measurement processing (1) program 54*a* is shown in the left column, the content of the measurement processing (2) program 54*b* is shown in the right column, and the content of the sampler operation processing program 54*c* is shown in the middle column. As for the sampler operation processing program 54*c*, the process content about a leading rack 101 is shown in the middle left column, and the process content about a trailing rack 101 is shown in the middle right column. The leading rack 101 is the rack 101 which is previously input from the before-analysis rack holding section 41 to the rack transportation section 43, and the trailing rack 101 is the rack 101 which is input afterwards in the state where the leading rack 101 remains in the rack transportation section 43. The numbers of states representing the positional relationships of the rack 101, the sample containers 100, and the sections shown in FIG. 15 to FIG. 18 correspond to the step numbers shown in FIG. 11 to FIG. 14. For example, the positional relationship of the rack 101, the sampler containers 100, and the sections in the state 13 shown in FIG. 15 is the positional relationship of the rack 101, the sample containers 100, and the sections in Step S13 shown in FIG. 11. As shown in FIG. 10 to FIG. 13, the measurement processing (1) program 54*a*, and the measurement processing (2) program 54*b*, and the sampler operation processing program 54*c* are executed substantially in combination with one another.

When the blood analyzer 1 is operated by a user, initialization of the sampler transportation device 4 is performed in Step S11. At this time, the protrusion piece 431*d* of the first belt 431 is moved to a predetermined position, and is set as a starting point position of the first belt 431. In Step S12, two protrusion pieces 431*d* are moved to a position (rack input position) opposed to the before-analysis rack holding section 41, and the leading rack 101 is input to a space between two protrusion pieces 431*d* of the first belt 431. The positional relationship of the rack 101, the sample containers 100, and the sections at this time is in the state 12 shown in FIG. 15. Hereinafter, the description of the positional relationships of the rack 101, the sample containers 100, and the sections in the states shown in FIG. 15 to FIG. 18 is omitted. In the embodiment, as shown in FIG. 15 to FIG. 18, the case where first to tenth sample containers 100 are accommodated in the rack 101 in order from the front to the rear with respect to the forward transportation direction will be described.

In Step S13, the leading rack 101 is moved toward the first measurement unit 2 (in the forward transportation direction). In Step S14, it is sensed by the presence sensing sensor 45 whether or not there is the first sample container 100 accommodated in the leading rack 101. In Step S15, it is sensed whether or not there is the second sample container 100. In Step S16, the barcode 100*a* of the first sample container 100 is read by the barcode reading section 44, and it is sensed whether or not there is the third sample container 100. The sensing result of the presence sensing sensor 45 and the barcode information read by the barcode reading sections 44, 256, and 356 are constantly transmitted to the host computer 6. In Step S17, the leading rack 101 is moved to the first extraction position (see FIG. 15) where the first sample container 100 is extracted from the leading rack 101 by the hand section 251 of the first measurement unit 2 (i.e., the first sample container 100 is transported to the first measurement unit 2). At this time, the barcode 101*a* of the rack 101 is read by the barcode reading section 44. In Step S1 8, the first sample container 100 is extracted from the leading rack 101 by the hand section 251 of the first measurement unit 2. At this time, the leading rack 101 is stopped at the position where the first sample container 100 corresponds to the first extraction position. In Step S19, in the first measurement unit 2, the sample of the first sample container 100 gripped by the hand section 251 is stirred, and the leading rack 101 from which the first sample container 100 is extracted is moved in the backward transportation direction opposite to the forward transportation direction.

In Step S20, in the first measurement unit 2, the first sample container 100 is set at the sample set section 255*a*, the barcode 100*a* of the second sample container 100 of the leading rack 101 is read, and it is sensed whether or not there is the fourth sample container 100. In Step S21, in the first measurement unit 2, the barcode 100*a* of the first sample container 100 is read by the barcode reading section 256. In Step S22, the first sample container 100 set at the sample set section 255*a* is clamped in contact with a restriction section (not shown), and an airtight cap of the sample container 100 is pricked and penetrated with a needle (not shown) of the sample suction section 21. At this time, the leading rack 101 is moved to the second extraction position (see FIG. 14) where the second sample container 100 is extracted from the leading rack 101 by the hand section 351 of the second measurement unit 3

(i.e., the second sample container 100 is transported to the second measurement unit 3). The reading of the barcode 100a of the sample container 100 performed by the barcode reading sections 256 and 356 is performed for check of the reading performed by the barcode reading section 44. In Step S23, the suction of the sample in the first sample container 100 is performed by the sample suction section 21 in the first measurement unit 2, and the second sample container 100 is extracted from the leading rack 101 by the hand section 351 of the second measurement unit 3. At this time, the leading rack 101 is stopped so that the second sample container 100 comes to the second extraction position (see FIG. 15) where the second sample container 100 is extracted by the hand section 351.

In Step S24, in the first measurement unit 2, the first sample container 100 is extracted from the sample set section 255a by the hand section 251, and sample preparation, stirring, and analysis are performed with respect to the sample sucked by the sample suction section 21. In addition, the sample in the second sample container 100 gripped by the hand section 351 in the second measurement unit 3 is stirred, and the leading rack 101 is moved in the forward transportation direction. In Step S25, in the second measurement unit 3, the second sample container 100 is set at the sample set section 355a, the barcode 100a of the third sample container 100 of the leading rack 101 is read, and it is sensed whether or not there is the fifth sample container 100. In Step S26, in the first measurement unit 2, the measurement for the sample in the first sample container 100 is completed. In the second measurement unit 3, the barcode 100a of the second sample container 100 is read by the barcode reading section 356. The barcode 100a of the fourth sample container 100 in the leading rack 101 is read, and it is sensed whether or not there is the sixth sample container 100. In the above description, the completion of the measurement for the sample means the completion of transmission of the measurement data in Step S4 shown in FIG. 10. That is, in Step S26, even when the measurement for the sample in the first sample container 100 is completed, the analysis process of the measurement data in Step S5 is not completed yet.

In Step S27, the second sample container 100 set at the sample set section 355a is clamped in contact with the restriction section 355b, and the airtight cap of the sample container 100 is pricked and penetrated with the needle (not shown) of the sample suction section 31. At this time, the leading rack 101 is moved in the forward transportation direction. In Step S28, the first sample container 100 is returned from the measurement unit 2 to the original container accommodating section 101b of the leading rack 101, and the suction of the sample in the second sample container 100 is performed by the sample suction section 31 in the second measurement unit 3. In Step S29, in the second measurement unit 3, the second sample container 100 is extracted from the sample set section 355a by the hand section 351, and sample preparation, stirring, and analysis are performed with respect to the sample sucked by the sample suction section 31. In addition, the leading rack 101 is moved in the forward transportation direction. In Step S30, the third sample container 100 is extracted from the leading rack 101 by the hand section 251 of the first measurement unit 2. At this time, the leading rack 101 is stopped at the position where the third sample container 100 corresponds to the first extraction position. In Step S31, in the first measurement unit 2, the sample of the third sample container 100 gripped by the hand section 251 is stirred, and the leading rack 101 is moved in the backward transportation direction. In the second measurement unit 3, the measurement for the sample in the second sample container 100 is completed.

In Step S32, in the first measurement unit 2, the third sample container 100 is set at the sample set section 255a. In Step S33, in the first measurement unit 2, the barcode 100a of the third sample container 100 is read by the barcode reading section 256. The second sample container 100 is returned from the second measurement unit 3 to the original container accommodating section 101b of the leading rack 101. In Step S34, the third sample container 100 is clamped, and the airtight cap of the sample container 100 is pricked and penetrated with the needle (not shown) of the sample suction section 21. The leading rack 101 is moved in the forward transportation direction. Also with respect to the following sample containers 100, the measurement process is performed in the first measurement unit 2 and the second measurement unit 3 in the same manner as the above description, and the transportation process of the leading rack 101 is performed in the sample transportation device 4. Herein, the same processes are repeated, and thus the drawings are simplified. In Step S35, a predetermined process is performed in each section. The positional relationship of the leading rack 101, the sample containers 100, and the sections corresponding to Step S23 to Step S28 in the repeated processes are shown in State 23a to State 28a of FIG. 16.

In Step S36, in the second measurement unit 3, the eighth sample container 100 is extracted from the sample set section 355a by the hand section 351, and sample preparation, stirring, and analysis are performed with respect to the sample sucked by the sample suction section 31. In addition, the leading rack 101 is moved in the forward transportation direction. In Step S37, the ninth sample container 100 is extracted from the leading rack 101 by the hand section 251 of the first measurement unit 2. At this time, the leading rack 101 is stopped at the position where the ninth sample container 100 corresponds to the first extraction position. In Step S38, in the first measurement unit 2, the sample of the ninth sample container 100 is stirred, and the leading rack 101 is moved in the backward transportation direction. In the second measurement unit 3, the measurement for the sample in the eighth sample container 100 is completed.

In Step S39, in the first measurement unit 2, the ninth sample container 100 is set at the sample set section 255a. In Step S40, in the first measurement unit 2, the barcode 100a of the ninth sample container 100 is read by the barcode reading section 256. The eighth sample container 100 is returned from the second measurement unit 3 to the original container accommodating section 101b of the leading rack 101. In addition, the protrusion piece 432d of the second belt 432 is moved to a predetermined position, and is set as a starting point position of the second belt 432. In Step S41, in the first measurement unit 2, the ninth sample container 100 is clamped, and the airtight cap of the sample container 100 is pricked and penetrated with the needle (not shown) of the sample suction section 21. The leading rack 101 is moved in the forward transportation direction. In Step S42, in the first measurement unit 2, the suction of the sample in the ninth sample container 100 is performed by the sample suction section 21, and the tenth sample container 100 is extracted from the leading rack 101 by the hand section 351 of the second measurement unit 3. At this time, the leading rack 101 is stopped so that the tenth sample container 100 comes to the second extraction position where the tenth sample container 100 is extracted by the hand section 351. In addition, two protrusion pieces 432d are moved to the rack input position, and the trailing rack 101 is input to a space between the two protrusion pieces 432*d* of the second belt 432.

In Step S43, in the first measurement unit 2, the ninth sample container 100 is extracted from the sample set section 255*a* by the hand section 251, and sample preparation, stirring, and analysis are performed with respect to the sample sucked by the sample suction section 21. In addition, the sample in the tenth sample container 100 gripped by the hand section 351 in the second measurement unit 3 is stirred, and the leading rack 101 and the trailing rack 101 are moved in the forward transportation direction. In Step S44, in the second measurement unit 3, the tenth sample container 100 is set at the sample set section 355*a*, and it is sensed by the presence sensing sensor 45 whether or not there is the first sample container 100 of the trailing rack 101. In Step S45, in the second measurement unit 3, the barcode 100*a* of the tenth sample container 100 is read by the barcode reading section 356, and it is sensed by the presence sensing sensor 45 whether or not there is the second sample container 100 of the trailing rack 101.

In Step S46, the tenth sample container 100 set at the sample set section 355*a* is clamped, and the airtight cap of the sample container 100 is pricked and penetrated with the needle (not shown) of the sample suction section 31. At this time, the barcode 100*a* of the first sample container 100 of the trailing rack 101 is read, and it is sensed whether or not there is the third sample container 100. In Step S47, the ninth sample container 100 is returned from the first measurement unit 2 to the original container accommodating section 101*b* of the leading rack 101, and the suction of the sample in the tenth sample container 100 is performed by the sample suction section 31 in the second measurement unit 3. In addition, the trailing rack 101 is moved in the forward transportation direction. At this time, the barcode 101*a* of the rack 101 is read by the barcode reading section 44. In Step S48, in the second measurement unit 3, the tenth sample container 100 is extracted from the sample set section 355*a* by the hand section 351, and sample preparation, stirring, and analysis are performed with respect to the sample sucked by the sample suction section 31. In addition, the leading rack 101 is moved in the forward transportation direction. In Step S49, the first sample container 100 is extracted from the trailing rack 101 by the hand section 251 of the first measurement unit 2. At this time, the trailing rack 101 is stopped at the position where the first sample container 100 corresponds to the first extraction position. As shown in State 49 of FIG. 17, the leading rack 101 is retreated at a position on the front side of the trailing rack 101, while the first sample container 100 is extracted from the trailing rack 101.

In Step S50, in the first measurement unit 2, the sample of the first sample container 100 of the trailing rack 101 is stirred, and the leading rack 101 and the trailing rack 101 are moved in the backward transportation direction. In the second measurement unit 3, the measurement for the sample in the tenth sample container 100 of the leading rack 101 is completed. In Step S51, in the first measurement unit 2, the first sample container 100 of the trailing rack 101 is set at the sample set section 255*a*, and the barcode 100*a* of the second sample container 100 of the trailing rack 101 is read, and it is sensed whether or not there is the fourth sample container 100. In Step S52, in the first measurement unit 2, the barcode 100*a* of the first sample container 100 of the trailing rack 101 is read by the barcode reading section 256. In addition, the tenth sample container 100 of the leading rack 101 is returned from the second measurement unit 3 to the original container accommodating section 101*b* of the leading rack 101. Meanwhile, the trailing rack 101 is retreated at a position on the rear side of the leading rack 101 as shown in State 52 of FIG. 18.

In Step S53, in the first measurement unit 2, the first sample container 100 is clamped, and the airtight cap of the sample container 100 is pricked and penetrated with the needle (not shown) of the sample suction section 21. The leading rack 101 and the trailing rack 101 are moved in the forward transportation direction. In Step S54, in the first measurement unit 2, the suction of the sample in the first sample container 100 is performed by the sample suction section 21, and the second sample container 100 is extracted from the trailing rack 101 by the hand section 351 of the second measurement unit 3. At this time, the leading rack 101 is retreated at the rack output position as shown in State 53 of FIG. 18. In Step S55, in the first measurement unit 2, the first sample container 100 is extracted from the sample set section 255*a* by the hand section 251, and sample preparation, stirring, and analysis are performed with respect to the sample sucked by the sample suction section 21. The sample in the second sample container 100 gripped by the hand section 351 in the second measurement unit 3 is stirred, and the trailing rack 101 is moved in the forward transportation direction.

In Step S56, in the second measurement unit 3, the second sample container 100 is set at the sample set section 355*a*, the barcode 100*a* of the third sample container 100 of the trailing rack 101 is read, and it is sensed whether or not there is the fifth sample container 100. The leading rack 101 is pressed by the rack output section 46, and is moved into the after-analysis rack holding section 42. In Step S57, in the first measurement unit 2, the measurement for the sample in the first sample container 100 is completed, and the barcode 100*a* of the second sample container 100 is read by the barcode reading section 356 in the second measurement unit 3. The barcode 100*a* of the fourth sample container 100 of the trailing rack 101 is read, and it is sensed whether or not there is the sixth sample container 100. Two protrusion pieces 431*d* of the first belt 431 is moved to a belt retreat position (opposite side of the rack transportation section 43) not to be an obstacle to movement of the trailing rack 101 by the second belt 432. Also with respect to the following sample containers 100, the measurement process is performed in the first measurement unit 2 and the second measurement unit 3 in the same manner as the above description, and the transportation process of the trailing rack 101 is performed in the sample transportation device 4. Herein, the same processes are repeated, and thus the drawings are simplified. In Step S58, a predetermined process is performed in each section.

In Step S59, in the first measurement unit 2, the suction of the sample in the ninth sample container 100 of the trailing rack 101 is performed by the sample suction section 21, and the tenth sample container 100 is extracted from the trailing rack 101 by the hand section 351 of the second measurement unit 3. At this time, the trailing rack 101 is stopped so that the tenth sample container 100 comes to the second extraction position where the tenth sample container 100 is extracted by the hand section 351.

In Step S60, in the first measurement unit 2, the ninth sample container 100 is extracted from the sample set section 255*a* by the hand section 251, and sample preparation, stirring, and analysis are performed with respect to the sample sucked by the sample suction section 21. The sample in the tenth sample container 100 gripped by the hand section 351 in the second measurement unit 3 is stirred, and the trailing rack 101 is moved in the forward transportation direction. In Step S61, in the second measurement unit 3, the tenth sample container 100 is set at the sample set section 355*a*. In Step S62, in the first measurement unit 2, the measurement for the sample in the ninth sample container 100 is completed, and the barcode 100*a* of the tenth sample container 100 is read by the barcode reading section 356 in the second measurement unit 3. In Step S63, in the second measurement unit 3, the tenth sample container 100 is clamped, and the airtight cap of the sample container 100 is pricked and penetrated with the needle (not shown) of the sample suction section 31. At this time, the trailing rack 101 is moved in the forward transportation direction.

In Step S64, the ninth sample container 100 is returned from the first measurement unit 2 to the original container accommodating section 101*b* of the trailing rack 101, and the suction of the sample in the tenth sample container 100 is performed by the sample suction section 31 in the second measurement unit 3. In Step S65, in the second measurement unit 3, the tenth sample container 100 is extracted from the sample set section 355*a* by the hand section 351, and sample preparation, stirring, and analysis are performed with respect to the sample sucked by the sample suction section 31. The trailing rack 101 is moved in the forward transportation direction. In Step S66, in the second measurement unit 3, the measurement for the sample in the tenth sample container 100 is completed. In Step S67, the tenth sample container 100 is returned from the second measurement unit 3 to the original container accommodating section 101*b* of the trailing rack 101. In Step S68, the trailing rack 101 is moved to the rack output position in the forward transportation direction. In Step S69, the trailing rack 101 is pressed by the rack output section 46 to be moved into the after-analysis rack holding section 42, and the operation is completed. As described above, a series of operations of the first measurement unit 2, the second measurement unit 3, and the sample transportation device 4 of the blood analyzer 1 according to the embodiment are performed. In the embodiment, two racks 101 are transported by way of example. When three or more racks 101 are transported, the third or later rack 101 is input to the rack transportation section 43 in the same manner as the case where the trailing rack 101 is input to the rack transportation section 43, and the same processes are performed in each section.

In the embodiment, as described above, the transportation device 4 is provided with the first belt 431 and the second belt 432 operable to transport the plurality of sample containers 100 to the first measurement unit 2 and the second measurement unit 3 by transporting the rack 101 to the transportation device 4 on the transportation path, and the first belt 431 and the second belt 432 are operable to move the rack 101 independently from each other, thereby transporting the plurality of racks 101 on the transportation path independently from each other. Accordingly, it is possible to suppress that the movement of one rack 101 is restricted by the movement of the other rack 101. Therefore, it is possible to efficiently distribute the plurality of racks 101 to the first measurement unit 2 and the second measurement unit 3. With such a configuration, it is not necessary that the second rack 101 pass the first rack 101. Accordingly, it is not necessary to provide the measurement unit with an acceptance section of the rack 101 or to provide a rack passing line and a rack slider. Therefore, it is possible to make the blood analyzer 1 compact.

In the embodiment, the first belt 431 and the second belt 432 are configured to transport the plurality of sample containers 100 accommodated in the rack 101 to the first measurement unit 2 and the second measurement unit 3, respectively. Accordingly, it is possible to distribute the samples in the plurality of sample containers 100 accommodated in the same rack 101 to the different two measurement units, and thus it is possible to efficiently perform the analysis processes of the samples.

In the embodiment, the transportation device 4 is provided with the after-analysis rack holding section 42 for holding the rack 101 accommodating the sample containers 100 containing the samples after the samples are measured by the first measurement unit 2 or the second measurement unit 3, and the rack output section 46 for outputting the after-analysis rack from the rack output position on the transportation path to the after-analysis rack holding section 42. The transportation device 4 is operable to feed the next new rack 101 from the before-analysis rack holding section 41 to the rack input position on the transportation path by the rack input section 411, before the rack 101 is output from the rack output position on the transportation path to the after-analysis rack holding section 42. With such a configuration, it is possible to more promptly feed the rack 101 onto the transportation path, as compared with the case where the next new rack 101 is fed from the before-analysis rack holding section 41 to the transportation path after the rack 101 is output from the transportation path to the after-analysis rack holding section 42. Therefore, the transportation device 4 can more promptly transport the sample containers 100 accommodated in the rack 101 to the two measurement units. As a result, it is possible to efficiently perform the analysis processes of the samples.

In the embodiment, the protrusion piece 431*d* of the first belt 431 is configured to move from the rack output position to the rack input position by passing through the downside of the first belt 431, and the protrusion piece 432*d* of the second belt 432 is configured to move from the rack output position to the rack input position by passing through the downside of the second belt 432. Accordingly, even when the rack 101 is placed on one belt of the first belt 431 and the second belt 432, it is possible to move the protrusion piece of the other belt from the rack output position to the rack input position, without coming into contact with the rack 101 placed on one belt.

It should be considered that the disclosed embodiment is only an example in all aspects and is not restrictive. The scope of the invention is not represented by the description of the embodiment but is represented by Claims, and the scope includes all modifications within the means and scope equivalent to Claims.

For example, in the embodiment, the blood analyzer is described as an example of the analyzer, but the invention is not limited thereto. The invention may be applied to any other analyzer provided with a plurality of measurement units.

In the embodiment, the transportation device is configured to transport the plurality of sample containers accommodated in one rack to the different measurement units, but the invention is not limited thereto. The transportation device may be configured to transport all of the plurality of sample containers accommodated in one rack to one measurement unit.

In the embodiment, each measurement unit is provided with the stirring section to stir the samples by way of example, but the invention is not limited thereto. The invention may be applied to an analyzer (e.g., biochemistry analyzer and urine analyzer, etc.) which does not stir the samples. In this case, the samples may be sucked from the sample containers accommodated in the rack by moving the sample suction section, without providing the sample container transportation section.

In the embodiment, the first sample container accommodated in the rack is transported to the first measurement unit, and the second sample container is transported to the second measurement unit by way of example, but the invention is not limited thereto. The first sample container may be transported to the second measurement unit, and the second sample container may be transported to the first measurement unit.

In the embodiment, the control device is provided with one control unit by way of example, but the invention is not limited thereto. The first measurement unit and the second measurement unit may be provided with control units, respectively. In addition, these control units may be mounted on the first measurement unit and the second measurement unit, respectively.

In the embodiment, the first measurement unit and the second measurement unit are the same type of measurement units by way of example, but the invention is not limited thereto. The first measurement unit and the second measurement unit may be the different types of measurement devices (e.g., blood cell count device, smear producing device, immune measurement device, biochemistry measurement device, etc.).

In the embodiment, the transportation device is provided with the transportation section using the first belt and the second belt by way of example, but the invention is not limited thereto. The transportation device may be provided with any other transportation section capable of transporting two racks independently from each other on the transportation path. For example, protrusion piece capable of being input and output from the downside of the transportation path to the upside of the transportation path may be provided, and the rack may be transported in a state where the protrusion piece is taken out (protruded) on the transportation path by moving in the transportation direction.

Figure 19:
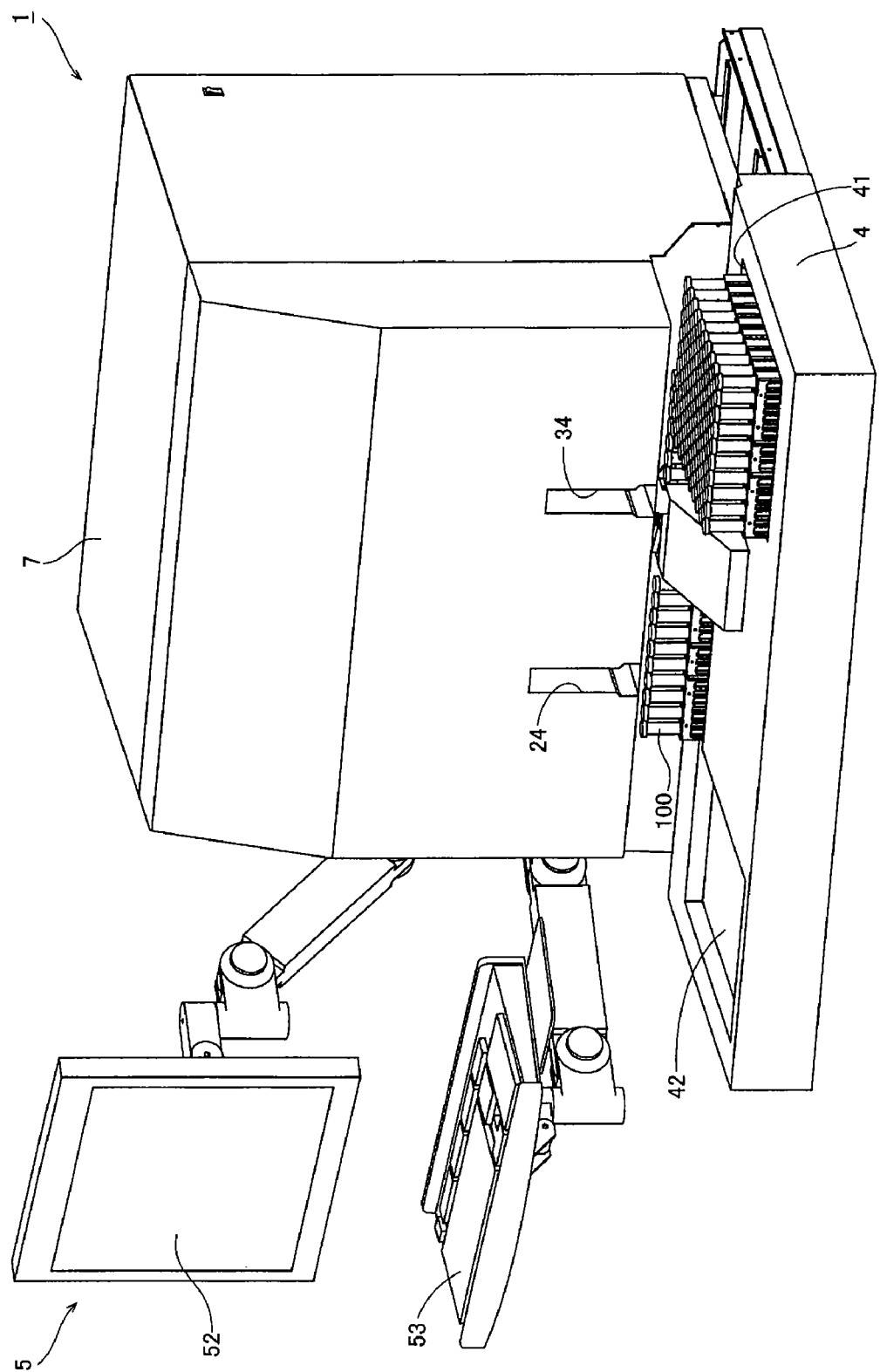
FIG. 19 is a diagram for explaining a modified example of the blood analyzer according to the embodiment of the invention.

In the embodiment, the first measurement unit and the second measurement unit are accommodated in the independent and separate housings, respectively, by way of example (see FIG. 1), but the invention is not limited thereto. As shown in FIG. 19, the first measurement unit and the second measurement unit may be accommodated together in one housing 7.

In the embodiment, the first measurement unit and the second measurement unit are disposed in the mirror shape which is symmetric with respective to the border line by way of example, but the invention is not limited thereto. The first measurement unit and the second measurement unit having the completely same shape may be disposed adjacent to each other.

In the embodiment, all of ten sample containers are accommodated in the rack by way of example, but the invention is not limited thereto. The invention may be applied to a case where some of ten sample containers are not accommodated. For example, when there is no sample container accommodated in the second position of the rack, the analysis process may be performed by considering the sample container accommodated in the third position as the second sample container.

What is claimed is:

1. An analyzer for analyzing samples in sample containers accommodated in a rack, the analyzer comprising:
a first measurement unit for measuring samples;
a second measurement unit for measuring samples; and
a transportation device operable to transport a plurality of sample containers accommodated in a first rack and containing samples and a plurality of sample containers accommodated in a second rack and containing samples, to the first measurement unit and the second measurement unit,
wherein the transportation device comprises a first transportation member operable to transport the plurality of sample containers on the first rack to the first measurement unit and the second measurement unit by transporting the first rack on a transportation path, and a second transportation member operable to transport the plurality of sample containers on the second rack to the first measurement unit and the second measurement unit by transporting the second rack on the transportation path independently from movement of the first rack,
the first transportation member comprises a first belt on which the first rack is placed,
the second transportation member comprises a second belt on which the second rack is placed and which is disposed parallel to the first belt, and
the transportation device further comprise a first driving section for driving the first belt and a second driving section for driving the second belt.

2. The analyzer according to claim 1, wherein the first belt comprises a first rack moving section coming into contact with the first rack and moving the first rack in a direction of movement of the first belt when the first belt is moved, and
wherein the second belt comprises a second rack moving section coming into contact with the second rack and moving the second rack in a direction of movement of the second belt when the second belt is moved.

3. The analyzer according to claim 2, wherein the first rack moving section comprises a first contact section coming into contact with an end section opposite to one direction of the first rack and moving the first rack in one direction when the first belt is moved in one direction, and a second contact section coming into contact with an end section opposite to the other direction of the first rack and moving the first rack in the other direction when the first belt is moved in the other direction opposite to one direction, and
wherein the second rack moving section comprises a third contact section coming into contact with an end section opposite to one direction of the second rack and moving the second rack in one direction when the second belt is moved in one direction, and a fourth contact section coming into contact with an end section opposite to the other direction of the second rack and moving the second rack in the other direction when the second belt is moved in the other direction opposite to one direction.

4. The analyzer according to claim 3, wherein the transportation device further comprises a before-analysis rack holding section for holding the first rack and the second rack accommodating sample containers containing samples before the samples are measured by the first measurement unit or the second measurement unit, and a before-analysis rack feeding section for feeding the first rack and the second rack from the before-analysis rack holding section to a rack feeding position of the transportation path, and
wherein the analyzer further comprises a transportation controller for controlling the before-analysis rack feeding section, and the first driving section, and the second driving section to feed the first rack to between the first contact section and the second contact section and to feed the second rack to between the third contact section and the fourth contact section.

5. The analyzer according to claim 4, wherein the transportation device further comprises an after-analysis rack holding section for holding an after-analysis rack accommodating sample containers containing samples after the samples are measured by the first measurement unit or the second measurement unit, and an after-analysis rack feeding section for feeding the after-analysis rack from a rack output position of the transportation path to the after-analysis rack holding section, and wherein the transportation controller controls the before-analysis rack feeding section and the after-analysis rack feeding section to feed the first rack or the second rack from the before-analysis rack holding section to the rack feeding position of the transportation path, before the after-analysis rack is fed from the rack output position of the transportation path to the after-analysis rack holding section.

6. The analyzer according to claim 2, wherein the first rack moving section is configured to move from a first position to a second position on the transportation path by passing through a downside of the first belt opposite to an upside of the first belt on which the first rack is placed, and wherein the second rack moving section is configured to move from a third position to a fourth position on the transportation path by passing through a downside of the second belt opposite to an upside of the second belt on which the second rack is placed.

7. The analyzer according to claim 1, wherein the first belt and the second belt are disposed adjacent and parallel to each other in a direction perpendicular to the transportation direction on the transportation path.

8. The analyzer according to claim 1, wherein a total width of the first belt and the second belt is a width allowing only one rack of the first rack and the second rack to pass.

9. An analyzer for analyzing samples in sample containers accommodated in a rack, the analyzer comprising:
- a first measurement unit for measuring samples;
- a second measurement unit for measuring samples; and
- a transportation device operable to transport a plurality of sample containers accommodated in a first rack and containing samples and a plurality of sample containers accommodated in a second rack and containing samples, to the first measurement unit and the second measurement unit, wherein the transportation device comprises a first transportation member operable to transport the plurality of sample containers on the first rack to the first measurement unit and the second measurement unit by transporting the first rack on a transportation path, and a second transportation member operable to transport the plurality of sample containers on the second rack to the first measurement unit and the second measurement unit by transporting the second rack on the transportation path independently from movement of the first rack, and wherein each of the first transportation member and the second transportation member is operable to transport sample containers in a forward direction from the first measurement unit to the second measurement unit and in a backward direction from the second measurement unit to the first measurement unit.

10. A transportation device
operable to transport a plurality of sample containers accommodated in a first rack and containing samples and a plurality of sample containers accommodated in a second rack and containing samples, to a first measurement unit and a second measurement unit, the transportation device comprising:
- a first transportation member operable to transport the plurality of sample containers on the first rack to the first measurement unit and the second measurement unit by transporting the first rack on a transportation path; and
- a second transportation member independently operable from the first transportation member and configured to transport the plurality of sample containers on the second rack to the first measurement unit and the second measurement unit by transporting the second rack on the transportation path independently from movement of the first rack, wherein the first transportation member comprises a first belt on which the first rack is placed,
wherein the second transportation member comprises a second belt on which the second rack is placed and which is disposed parallel to the first belt,
wherein the transportation device further comprises a first driving section for driving the first belt and a second driving section for driving the second belt.

* * * * *